United States Patent [19]
Montana et al.

[11] Patent Number: 5,994,312
[45] Date of Patent: Nov. 30, 1999

[54] PEPTIDYL COMPOUNDS

[75] Inventors: John Montana; Andrew Douglas Baxter; David Alan Owen; Robert John Watson; Neil Phillipson, all of Cambridge, United Kingdom

[73] Assignee: Darwin Discovery, Ltd., United Kingdom

[21] Appl. No.: 09/124,877

[22] Filed: Jul. 30, 1998

Related U.S. Application Data

[63] Continuation of application No. 08/539,578, Oct. 5, 1995, abandoned.

[30] Foreign Application Priority Data

Oct. 5, 1994 [GB] United Kingdom .................. 9420057
Mar. 10, 1995 [GB] United Kingdom .................. 9504907
Mar. 10, 1995 [GB] United Kingdom .................. 9509431

[51] Int. Cl.[6] .................................................. A61K 38/00
[52] U.S. Cl. ........................ 514/19; 514/616; 564/153; 564/154; 435/212; 424/184.1; 730/868
[58] Field of Search .................................. 564/153–154; 514/616, 19; 435/212; 424/184.1; 530/868

[56] References Cited

U.S. PATENT DOCUMENTS

| | | | |
|---|---|---|---|
| 4,146,611 | 3/1979 | Ondetti et al. ............................ | 514/19 |
| 4,235,885 | 11/1980 | Sundeen et al. ........................ | 514/562 |
| 4,263,293 | 4/1981 | Sundeen et al. ....................... | 514/237.8 |
| 4,382,081 | 5/1983 | Sundeen et al. ......................... | 514/18 |
| 4,511,504 | 4/1985 | McCullagh et al. ..................... | 560/29 |
| 5,387,610 | 2/1995 | Gray et al. .............................. | 514/575 |
| 5,455,262 | 10/1995 | Schwartz et al. ....................... | 514/418 |

FOREIGN PATENT DOCUMENTS

| | | |
|---|---|---|
| 0524553 | 1/1993 | European Pat. Off. . |
| 0524553 A1 | 1/1993 | European Pat. Off. . |
| 8806890 | 9/1988 | WIPO . |
| 9506031 | 3/1995 | WIPO . |
| 9513289 | 5/1995 | WIPO . |

OTHER PUBLICATIONS

Fournie–Zaluski et al., Eur. J. Biochem. vol. 139, 267, 1984.

Dayhoff et al., Atlas of Protein Sequence and Structure, vol. 5, Dayhoff (ed.), 1975.

Fournie–Zaluski, M. et al. (1984) "Differences in the structural requirements for selective interaction with neutral metalloendopeptidase (enkephalinase) or angiotensin–converting enzyme". Eur. J. Biochem. 139: 267–274.

Blumberg, S., Tauber, Z. (1983) "Inhibition of metalloendopeptidases by 2–mercaptoacetyl–dipeptides". Eur. J. Biochem. 136: 151–154.

Dayhoff, M.O. et al. (1992) Atlas of Protein Sequence and Structure, vol. 5. National Biomedical Research Foundation.

*Primary Examiner*—Bennett Celsa
*Attorney, Agent, or Firm*—Saliwanchik, Lloyd & Saliwanchik

[57] ABSTRACT

Compounds of general formula (I):

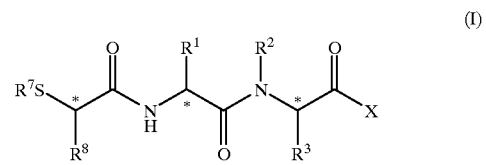

have utility as inhibitors of matrix metalloproteinases and TNF.

24 Claims, No Drawings

PEPTIDYL COMPOUNDS

CROSS REFERENCE TO RELATED APPLICATION

This application is a continuation of application Ser. No. 08/539,578, filed Oct. 5, 1995 (Abn).

FIELD OF THE INVENTION

This invention relates to a novel class of peptidyl derivatives, to processes for their preparation, and to their use in medicine.

BACKGROUND TO THE INVENTION

In normal tissues, cellular connective tissue synthesis is offset by extracelluar matrix degradation, the two opposing effects existing in dynamic equilibrium. Degradation of the matrix is brought about by the action of proteinases released from resident connective tissue cells and invading inflammatory cells, and is due, in part, to the activity of at least three groups of metalloproteinases. These are the collagenases (interstitial collagenase, MMP-1; PMN collagenase, MMP-8, collagenase-3, MMP13), the gelatinases (gelatinase A, MMP-2, 72 kDa-gelatinase, Type IV collagenase; gelatinase B, MMP-9, 92 kDa-gelatinase, Type IV collagenase) and the stromelysins (proteoglycanase, MMP-3, stromelysin-1, transin; stromelysin-2, MMP:10; stromelysin-3, MMP:11). Normally these catabolic enzymes are tightly regulated at the level of their synthesis and secretion and also at the level of their extracellular activity, the latter through the action of specific inhibitors, such as TIMP (tissue inhibitors of metalloproteinase), which form inactive complexes with metalloproteinases, and more general proteinase inhibitors such as $a_2$-macroglobulins.

The accelerated, uncontrolled breakdown of connective tissues by metalloproteinase catalysed resorption of the extracellular matrix is a feature of many pathological conditions such as rheumatoid arthritis, osteoarthritis, septic arthritis, corneal, epidermal or gastric ulceration; tumour metastasis or invasion; periodontal disease, proteinuria, coronary thrombosis associated with atherosclerotic plaque rupture and bone disease. The inhibitors claimed herein may also be useful in preventing the pathological squaelae following a traumatic injury that could lead to a permanent disability. These compounds may also have utility as a means for birth control by preventing ovulation or implantation. It can be expected that the pathogenesis of such diseases is likely to be modified in a beneficial manner by the administration of metalloproteinase inhibitors and numerous compounds have been suggested for this purpose [for a general review see R C Wahl, et al Ann. Rep, Med. Chem. 25:175–184, Academic Press Inc., San Diego (1990)].

A number of small peptide like compounds which inhibit metalloproteinases have been described. Perhaps the most notable of these are those relating to angiotensin converting enzyme (ACE) where such agents act to block the conversion of the decapeptide angiotensin I to angiotensin II, a potent pressor substance. Compounds of this type are described in EP-A-0012401. Also, related mercaptoamide peptidyl derivatives have shown ACE inhibitor activity in vitro and in vivo (H N Weller et al (1984), Biochem Biophys. Res. Comm., 125 (1):82–89).

TNFα is a cytokine which is produced initially as a cell-associated 28 kD precursor. It is released as an active, 17 kD form (D-M Jue et al, (1990) Biochemistry, 29:8371–8377), which can mediate a large number of deleterious effects in vivo. When administered to animals or humans it causes inflammation, fever, cardiovascular effects, haemorrhage, coagulation and acute phase responses, similar to those seen during acute infections and shock states. Chronic administration can also cause cachexia and anorexia. Accumulation of excessive TNFα can be lethal. There is considerable evidence from animal model studies that blocking the effects of TNFα with specific antibodies can be beneficial in acute infections, shock states, graft versus host reactions and autoimmune disease. TNFα is also an autocrine growth factor for some myelomas and lymphomas and can act to inhibit normal heamatopoiesis in patients with these tumours.

Preventing the production or action of TNFα is, therefore, predicted to be a potent therapeutic strategy for many inflammatory, infectious, immunological or malignant diseases. These include, but are not restricted to, septic shock, haemodynamic shock and sepsis syndrome (Mathison et al (1988) J. Clin. Invest. 81:1925–1937; Miethke et al (1992), J. Exp. Med. 175:91–98), post-ischaemic reperfusion injury, malaria (Grau et al (1989), Immunol. Rev. 112:49–70); mycobacterial infection (Barnes et al (1992) Infect. Imm. 60:1441-6), meningitis, psoriasis, congestive heart failure, fibrotic disease, cachexia, graft rejection, cancer, autoimmune disease, rheumatoid arthritis, multiple sclerosis, radiation damage, toxicity following administration of immunosuppressive monoclonal antibodies such as OKT3 or CAMPATH-1 and hyperoxic alveolar injury.

Current clinical anti-TNFα strategies involve the use of corticosteroids such as dexamethasone, and the use of cyclosporin-A or FK506, which are non-specific inhibitors of cytokine gene transcription. Phosphodiesterase inhibitors such as pentoxyfilline have been shown to be more specific inhibitors of TNFα gene transcription (Endres S. (1991) Immunol. 72:56–60, Schandene et al (1992), Immunol. 76:30–34, Alegre M L, et al (1991); Transplantation 52:674–679, Bianco et al (1991) Blood 78:1205–1221). Thalidomide has also been shown to inhibit TNFα production by leucocytes (Sampajo et al (1991), J. Exp. Med. 173:699–703). In experimental settings, anti-TNFα monoclonal antibodies, soluble TNF receptors and soluble TNF receptor/immunoadhesins have been shown to specifically inhibit the effects of TNFα action (Bagby et al (1991) J. Infect. Dis. 163:83–88, Charpentier et al. (1991) Pressemed. 20:2009–2011, Silva et al (1990) J. Infect. Dis. 162:421–427; Franks et al (1991) Infect. Immun. 59:2609–2614, Tracey et al (1987) Nature 330:662–664; Fischer et al (1992) PNAS USA in press, Lesslauer et al (1991) Eur. J. Immunol. 21:2883–2886, Ashkenazi et al (1991) PNAS USA 88:10535–10539).

It has recently been shown that the effects of TNF are mediated by two peptides, TNFα and TNFβ. Although these peptides have only 30% homology with each other, they activate the same receptors and are encoded by immediately adjacent genes. As used herein, the term tumour necrosis factor or TNF therefore means tumour necrosis factor α and peptides having a high degrees of sequence homology with, or substantially similar physiological effects to, TNFα, for example TNFβ. One of the objectives of the present invention is to provide compounds which substantially inhibit the release of TNF from cells, and therefore may be used in the treatment of conditions mediated by TNF. Such uses include, but are not limited to, the treatment of inflammation, fever, cardiovascular effects, haemorrhage, coagulation and acute phase response, cachexia and anorexia, acute infections, shock states, graft versus host reactions and autoimmune disease.

Compounds which have the property of inhibiting the action of metalloproteinases involved in connective tissue breakdown such as collagenase, stromelysin and gelatinase have been shown to inhibit the release of TNF both in vitro and in vivo (A J H Gearing et al (1994), Nature, 370:555–557; G M McGeehan et al (1994), Nature, 370:558–561; M J Crimmin et al, WO 93/20047). All of these reported inhibitors contain a hydroxamic acid zinc binding group.

It is, therefore, a further object of this invention to provide compounds which, in addition to inhibiting TNF release, also inhibit the action of MMPs, and hence may be used in the treatment of patients who suffer from conditions mediated by TNF and/or MMPs.

As appreciated by those of skill in the art the significant proportion of homology between human fiberblast collagenase, stromelysin and gelatinase leads to the possibility that a compound that inhibits one enzyme may to some degree inhibit all of them.

Compounds that inhibit collagenase, which possess structural portions akin to those of the instant invention include those encompassed by U.S. Pat. No. 4,511,504 issued Apr. 16, 1985; U.S. Pat. No. 4,568,666, issued Feb. 4, 1986.

Compounds of related structure that are claimed to inhibit stromelysin (proteoglycanase) are encompassed by U.S. Pat. No. 4,771,037, issued Sep. 13, 1988. The applicants believe that stromelysin and collagenase inhibitors have utility in preventing articular cartilage damage associated with septic arthritis. Bacterial infections of the joints can elicit an inflammatory response that may then be perpetuated beyond what is needed for removal of the infective agent resulting in permanent damage to structural components. Bacterial agents have been used in animal models to elicit an arthritic response with the appearance of proteolytic activities. See J. P. Case et al (1989), J. Clin. Invest., 84:1731–40; R. J. Williams et al (1990), Arth. Rheum., 33:533–41.

The applicants also believe that inhibitors of stromelysin, collagenase and gelatinase will be useful to control tumour metastasis, optionally in combination with current chemotherapy and/or radiation. See L. M Matrisian et al (1986), Proc. Natl. Acad. Sci., USA, 83:9413-7; S. M. Wilhelm et al (1987), Ibid. 84:6725–29; Z. Werb et al (1989), J. Cell Biol., 109:872–889; L. A. Liotta et al (1983), Lab. Invest., 49:636–649; R. Reich et al in Metatasis; Ciba Foundation Symposium, Wiley, Chicester, 1988, pp. 193–210.

Secreted proteinases such as stromelysin, collagenase and gelatinase play an important role in processes involved in the movement of cells during metastasic tumour invasion. Indeed, there is also evidence that the matrix metalloproteinases are overexpressed in certain metastatic tumour cell lines. In this context, the enzyme functions to penetrate underlying basement membranes and allow the tumour cell to escape from the site of primary tumour formation and enter the circulation. After adhering to blood vessel walls, the tumour cells use these same metalloproteinases to pierce underlying basement membranes and penetrate other tissues, thereby leading to tumour metastasis. Inhibition of this process would prevent metastasis and improve the efficacy of current treatments with chemotherapeutics and/or radiation. These inhibitors should also be useful for controlling periodontal diseases, such as gingivitis. Both collagenase and stromelysin activities have been isolated from fibroblasts derived from inflamed gingiva (V. J. Uitto et al (1981), J. Periodontal Res., 16:417–424). Enzyme levels have been correlated to the severity of gum disease; C. M. Overall et al (1987), J. Periodontal Res., 22:81–88.

Proteolytic processes have also been observed in the ulceration of the cornea following alkali burns (S. I. Brown et al (1969), Arch. Opthalmol., 81:370–373). Mercapto-containing peptides do inhibit the collagenase isolated from alkali-burned rabbit cornea (F. R. burns et al (1989), Invest. Opthalmol, 30:1569–1575). Treatment of alkali-burned eyes or eyes exhibiting corneal ulceration as a result of infection with inhibitors of these metalloendoproteinases in combination with sodium citrate or sodium ascorbate and/or antimicrobials may be effective in preventing developing corneal degradation.

Stromelysin has been implaced in the degradation of structural components of the glomerular basement membrane (GBM) of the kidney, the major function of which is to restrict passage of plasma proteins into the urine (W. H. Baricos et al (1989), Biochem. J., 254:609–612). Proteinuria, a result of glomerular disease, is excess protein in the urine caused by increased permeability of the GBM to plasma proteins. The underlying causes of the increased GBM permeability are unknown, but proteinases including stromelysin may play an important role in glomerular diseases. Inhibition of this enzyme may alleviate the proteinura associated with kidney malfunction.

It is suggested that inhibition of stromelysin activity may prevent the rupturing of atherosclerotic plaques leading to coronary thrombosis. The tearing or rupture of atherosclerotic plaques is the most common event initiating coronary thrombosis. Destabilisation and degradation of the connective tissue matrix surrounding these plaques by proteolytic enzymes or cytokines released by infiltrating inflammatory cells has been proposed as a cause of plaque fissuring. Such tearing of these plaques can cause an acute thrombolytic event as blood rapidly flows out of the blood vessel. High levels of stromelysin RNA message have been found to be localised to individual cells in atherosclerotic plaques removed from heart transplant patients at the time of surgery (A. M. Henney et al (1991), Proc. Nat'l. Acad. Sci. USA, 88:8154–8158). Inhibition of stromelysin by these compounds may aid in preventing or delaying the degradation of the connective tissue matrix that stabilises the atherosclerotic plaques, thereby preventin events leading to acute coronary thrombosis.

It is also believed that specific inhibitors of stromelysin and collagenase should be useful as birth control agents. There is evidence that expression of metalloproteinases, including stromelysin and collagenase, is observed in unfertilised eggs and zygotes and at further cleavage stages and increased at the blastocyst stage of fetal development and with endoderm differentiation (C. A. Brenner et al (1989), Genes & Develop., 3:848–59). By analogy to tumour invasion, a blastocyst may express metalloproteinases in order to penetrate the extracelluar matrix of the uterine wall during implantation. Inhibition of stromelysin and collagenase during these early development processes should presumably prevent normal embryonic development and/or implantation in the uterus. Such intervention would constitute a novel method of birth control. In addition there is evidence that collagenase is important in ovulation processes. In this example, a covering of collagen over the apical region of the follicle must be penetrated in order for the ovum to escape. Collagenase has been detected during this process and an inhibitor has been shown to be effective in preventing ovulation (J. F. Woessner et al (1989), Steroids, 54:491–499). There may also be a role for stromelysin activity during ovulation (C. K. L. Too et al (1984), Endocrin., 115:1043–1050).

Collagenolytic and stromelysin activity have also been observed in dystrophic epidermolysis bullosa (A. Kronberger et al (1982), J. Invest. Dermatol., 79:208–211; D. Sawamura et al (1991), Biochem. Biophys. Res. Commun., 184:1003–8). Inhibition of metalloendoproteinases should limit the rapid destruction of connective components of the skin.

In addition to extracelluar matrix comprising structural components, stromelysin can degrade other in vivo substrates including the inhibitors $a_1$-proteinase inhibitor and may therefore influence the activities of other proteinases such as elastase (P. G. Winyard et al (1991), FEBS Letts., 279, 1:92–94). Inhibition of the matrix metalloendoproteinases may potentiate the antiproteinase activity of these endogenous inhibitors.

From recent publications it is evident that several new enzymes of the MMP family have been identified, some of which maybe important in disease. Collagenase 3, an enzyme unique to breast carcinoma cells may have utility in breast cancer (J M P Freije et al (1994), J. Biol. Chem., 269 (24): 16766–16773), whilst MT-MMP, another member of the MMP family has been shown to be a key enzyme in the activaton of gelatinase A (H Sato et al (1994), Nature, 370:61–65). Gelatinase A is an important enzyme in the growth and metastasis of tumours (such as defined above).

The degradation of b-Amyloid Precusor Protein (APP) has been shown to generate amyloid plaques, a major constitutent of the senile plaques, found in patients with Alzheimers Disease (AD). Two recent publications have identified metalloproteinase enzymes that cleave APP to the amyloid plaque (CR Abraham et al (1994), Biochemistry, 33:192–199; G Huber et al (1994), Biochem. Biophys. Res. Comm., 201 (1):45–53).

As appreciated by those of skill in the art, the significant proportion of homology between these new enzymes and other MMPs leads to the possibility that a compound that inhibits one enzyme may to some degree inhibit these new enzymes. Therefore, inhibitors encompassed in this invention may be useful in the diseases in which these new enzymes are implicated.

SUMMARY OF THE INVENTION

The invention encompasses novel mercaptoalkylpeptidyl compounds of formula (I) which are useful inhibitors of matrix metalloproteinases and/or TNFα mediated diseases including degenerative diseases (such as defined above) and certain cancers.

In a first aspect of the invention there is provided a compound of general formula (I):

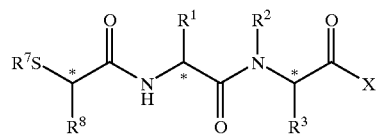

Wherein:
$R^1$ is $C_{1-6}$ alkyl, $C_{2-6}$ alkenyl, —$C_{1-6}$ alkyl-aryl, aryl, —$C_{1-6}$ alkyl-heteroaryl, heteroaryl or —$C_{1-6}$ alkyl-AR$^9$ where A represents O, NR$^9$ or S(O)$_m$ where m=0–2, and R$^9$ is H, $C_{1-4}$ alkyl, aryl, heteroaryl, —$C_{1-4}$ alkyl-aryl or —$C_{1-4}$ alkyl-heteroaryl; if A=NR$^9$ the groups R$^9$ may be the same or different;

$R^2$ is H or $C_{1-6}$ alkyl;

$R^3$ is [Alk]$_n$R$^6$ where Alk is $C_{1-6}$ alkyl or $C_{2-6}$ alkenyl and n is zeo or 1;

X is NR$^4$R$^5$ where either R$^4$ is hydrogen or $C_{1-6}$ alkyl optionally substituted by amino (NH$_2$), aryl, arylamino, protected amino, di($C_{1-6}$ alkyl)amino, mono($C_{1-6}$ alkyl) amino, $CO_2H$, protected carboxyl, carbamoyl, mono($C_{1-6}$ alkyl)carbamoyl or di($C_{1-6}$ alkyl)carbamoyl, and R$^5$ is hydrogen or $C_{1-6}$ alkyl; or NR$^4$R$^5$ forms a ring such as pyrrolidino, piperidino or morpholino;

$R^7$ is hydrogen or R$^{10}$CO where R$^{10}$ is $C_{1-4}$ alkyl, —$C_{1-4}$ alkyl-aryl, —$C_{1-4}$ alkyl-heteroaryl, cyclo($C_{3-6}$)alkyl, —$C_{1-4}$ alkyl-cyclo($C_{3-6}$)alkyl, $C_{2-6}$ alkenyl, —$C_{2-6}$ alkenyl-aryl, aryl or heteroaryl;

$R^8$ is aryl (substituted with R$^{11}$), heteroaryl (optionally substituted with R$^{11}$), $C_{1-4}$ alkyl-R$^{11}$, —$C_{1-4}$ alkyl-aryl (substituted with R$^{11}$), —$C_{1-4}$ alkyl-heteroaryl (optionally substituted with R$^{11}$), cyclo($C_{3-6}$)alkyl (optionally substituted with R$^{11}$), cyclo($C_{3-6}$)alkenyl (optionally substituted with R$^{11}$), —$C_{1-4}$ alkyl-cyclo($C_{3-6}$)alkyl (optionally substituted with R$^{11}$), or any of the three groups

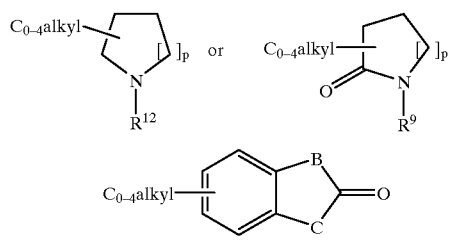

where p is 1 or 2 and B and C are independently selected for O, S, C(R$^9$)$_2$ and NR$^9$;

$R^6$ is AR$^9$, cyclo($C_{3-6}$)alkyl, cyclo($C_{3-6}$)alkenyl, $C_{1-6}$ alkyl, —$C_{1-6}$ alkoxy-aryl, benzyloxyaryl, aryl, heteroaryl, —$C_{1-3}$ alkyl-heteroaryl, —$C_{1-3}$ alkyl-aryl, —$C_{1-6}$ alkyl-COOR$^9$, —$C_{1-6}$ alkyl-NHR, CONHR, NHCO$_2$R, NHSO$_2$R or NHCOR, R being defined as for R$^{10}$;

$R^{11}$ is SO$_2$R$^{13}$, SR$^7$, SR$^9$, COR$^{13}$, N(R$^9$)$_2$, NR$^9$R$^{12}$, OR$^9$, succinimido or phthalimido;

$R^{12}$ is H or COR$^9$, CO$_2$R$^9$ (where R$^9$ is not H), CONHR$^9$ or SO$_2$R$^9$ (where R$^9$ is not H); and $R^{13}$ is OH, OC$_{1-4}$ alkyl, O-C$_{1-4}$ alkyl-aryl, N(R$^9$)$_2$ (in which the R$^9$s are the same or different), C$_{1-4}$ alkyl, aryl, heteroaryl, —$C_{1-4}$ alkyl-aryl or —$C_{1-4}$ alkyl-heteroaryl;

the compound being in the form of a non-salt, salt, solvate or hydrate. Preferred compounds of the invention include those in which, independently or in any combination have:

$R^1$ is $C_{1-6}$ alkyl or $C_{1-4}$ alkylAR$^9$ where A is S(O)$_m$, NR$^9$, or O and m=0,1 or 2, and $R^9$ is H, $C_{1-4}$ alkyl or aryl;

$R^2$ is H or $C_{1-4}$ alkyl;

$R^3$ is [Alk]$_n$R$^6$ where n=0 or 1, Alk is $C_{1-4}$ alkyl and R$^6$ is $C_{1-4}$ alkyl, $C_{1-3}$ alkylaryl, $C_{1-3}$ alkylheteroaryl or AR$^9$;

$R^4$ is H;

$R^5$ is H or $C_{1-6}$ alkyl;

NR$^4$R$^5$ may form a 5–7 membered ring such as a pyrrolidine, piperidine or morpholine;

$R^7$ is H or R$^{10}$CO where R$^{10}$ is $C_{1-4}$ alkyl;

$R^8$ is $C_{1-4}$ alkylR$^{11}$, $C_{1-4}$ alkenylR$^{11}$, Cyclo($C_{3-6}$) alkylR$^{11}$;

$R^{11}$ is COR$^{13}$, NR$^9$R$^{12}$, N(R$^9$)$_2$, succinimido or phthalimido, $R^{12}$ is COR$^9$, CO2R$^9$ (provided R9 is not H), or SO$_2$R$^9$ (provided R9 is not H); and R$^{13}$ is OH, OC$_{1-4}$ alkyl or N(R$^9$)$_2$;

Compounds of the invention have IC$_{50}$ values below 50 mM against the MMP enzymes and/or below 50 mM in the whole cell assay of TNF inhibition. It will be appreciated that the compounds according to the invention can contain one or more asymmetrically substituted carbon atoms, for example those marked with an asterisk in formula (1). The presence of one or more of these asymmetric centres in a compound of formula (1) can give rise to stereoisomers, and in each case the invention is to be understood to extend to all such stereoisomers, including enantiomers and diastereomers, and mixtures including racemic mixtures thereof. In the formulae herein, the ~ line is used at a potential asymmetric centre to represent the possibility of R- and S- configurations, the < line and the . . . line to represent a unique configuration at an asymmetric centre.

As used in this specification, alone or in combination, the term "$C_{1-6}$ alkyl" refers to a straight or branched chain alkyl moiety having from one to six carbon atoms, including for example, methyl, ethyl, propyl, isopropyl, butyl, t-butyl, pentyl, hexyl and the like.

The term "$C_{1-4}$ alkyl" refers to a straight or branched chain alkyl moiety having from one to four carbon atoms, including for example, methyl ethyl, propyl, isopropyl, butyl, t-butyl and the like.

The term "$C_{2-6}$ alkenyl" refers to a straight or branched chain alkyl moiety having two to six carbon atoms and having in addition one double bond, of either E or Z stereochemistry where applicable. This term would include for example, vinyl, 1-propenyl, 1- and 2-butenyl, 2-methyl-2-propenyl etc.

The term "cyclo($C_{3-6}$)alkyl" refers to a saturated alicyclic moiety having from three to six carbon atoms and includes for example cyclopropyl, cyclobutyl, cyclopentyl, cyclohexy and the like.

The term "cyclo($C_{3-6}$) alkenyl" refers to an alicyclic moiety having from three to six carbon atoms and having in addition one double bond. This term would include for example cyclopentenenyl or cyclohexenyl.

The term "aryl" means an optionally substituted phenyl or naphthyl group with the substituent(s) being selected, for example, from halogen, trifluoromethyl, $C_{1-6}$ alkyl, alkoxy, phenyl and the like. The term "halogen" means fluorine, chlorine, bromine or iodine.

The terms "protected amino" and "protected carboxy" mean amino and carboxy groups which are protected in a manner familiar to those skilled in the art. For example, an amino group can be protected by a benzyloxycarbonyl, tert-butoxycarbonyl, acetyl or like groups, or in the form of a phthalimido or like group. A carboxyl group can be protected in the form of a readily cleavable ester such as the methyl, ethyl, benzyl or tert-butyl ester.

The term "alkoxy" refers to a straight chain or branched chain alkoxy group containing a maximum of six carbon atoms, such as methoxy, ethoxy, propoxy, isopropoxy, butoxy, tert-butoxy and the like.

The term "$C_{0-4}$alkyl" refers to a bond or straight or branched chain alkyl moiety having from up to four carbon atoms, including for example, methyl, ethyl, propyl, isopropyl and the like.

The term "heteroaryl" refers to aromatic ring systems of five to ten atoms of which at least one atom is selected from the group, O, N or S.

Salts of compounds of formula (I) include pharmaceutically acceptable salts, for example acid addition salts derived from inorganic or organic acids, such as hydrochlorides, hydrobromides, p-toluenesulphonates, phosphates, sulphates, perchlorates, acetates, trifluoroacetates, propionates, citrates, malonates, succinates, lactates, oxalates, tartrates, and benzoates.

Salts may also be formed with bases. Such salts include salts derived from inorganic or organic bases, for example alkali metal salts such as magnesium or calcium salts, and organic amine salts such as morpholine, piperidine, dimethylamine, or dimethylamine salts.

When the "protected carboxy" group in compound of the invention is an esterified carbozyl group, it may be a metabolically labile ester of formula $CO_2R^{14}$ where $R^{14}$ may be an ethyl, benzyl, phenethyl, phenylpropyl, α- or β-naphthyl, 2,4-dimethylphenyl, 4-tert-butylphenyl, 2,2,2-trifluoroethyl, 1-(benzyloxy)benzyl, 1-(benxyloxy)ethyl, 2-methyl-1-propionyloxypropyl, 2,4,6-trimethylbenzyloxymethyl or pivaloyloxymethyl group.

Compounds of the general formula (I) may be prepared by any suitable method known in the art and/or by the following processes, which itself forms part of the invention.

According to a second aspect of the invention, there is provided a process for preparing a compound of general formula (I) as defined above. It will be appreciated that where a particular stereoisomer of formula (I) is required, the synthetic processes described herein may be used with the appropriate homochiral starting material and/or isomers may be resolved from mixtures using conventional separation techniques (e.g., HPLC).

The compounds according to the invention may be prepared by the following process. In the description and formulae below, the groups $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, A, B, C, and X are as defined above, except where otherwise indicated. It will be appreciated that functional groups, such as amino, hydroxyl, or carboxyl groups, present in the various compounds described below, and which it is desired to retain, may need to be in protected form before any reaction is initiated. In such instances, removal of the protecting group may be the final step in a particular reaction. Suitable protecting groups for such functionality apparent to those skilled in the art. For specific details see "Protective Groups in Organic Synthesis", Wiley Interscience, T W Greene, PGM Wuts. Thus a process for preparing compounds of general formula (I) comprises the steps of:

deprotecting (for example by hydrolysis) a compound of general formula (II)

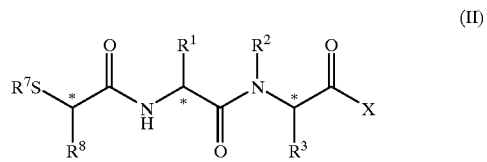

(II)

wherein $R^7$ represents a suitable protecting group (eg tert butyl or acetate). It will be appreciated that where a particular stereoisomer of formula (I) is required, this may be obtained by conventional resolution techniques such as high performance liquid chromatography. Where desired, however, appropriate homochiral starting materials may be used in the coupling reaction to yield a particular stereoisomer of formula (I). This is exemplified below.

Intermediates of general formula (II) may be prepared by coupling an acid of formula (III)

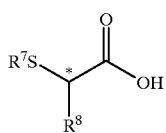

(III)

wherein $R^7$ and $R^8$ are as defined above, or an active derivative thereof, with an amine of formula (IV)

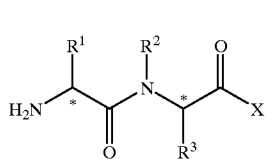

(IV)

Active derivatives of acids of formula (III) include for example acid anhydrides or acid halides, such as acid chlorides.

The coupling reaction may be performed using standard conditions for amination reactions of this type. Thus, the reaction may be achieved in a solvent, for example an inert organic solvent such as an ether, eg. a cyclic ether such as tetrahydrofuran, an amide eg. a substituted amide such as dimethyformamide, or a halogenated hydrocarbon such as dichlormethane at a low temperature eg. −30° C. to ambient temperature, such as −20° C. to 0° C., optionally in the presence of as base, eg. an organic base such as an amine, eg. triethylamine or a cyclic amine such as N-methylmorpholine. Where an acid of formula (III) is used, the reaction may additionally be performed in the presence of a condensing agent, for example a diimide such as N,N'-dicyclohexylcarbodiimide, advantageously in the presence of a triazole such as 1-hydroxybenzotriazole. Alternatively, the acid may be reacted with a chloroformate for example ethylchloroformate, prior to reaction with the amine of formula (IV).

The amine of general formula (IV) may be prepared by coupling an acid of formula (V), or an active derivative thereof

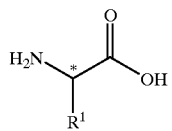

(V)

with an amine of formula (VI)

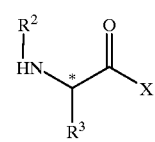

(VI)

followed by removal of any protecting groups.

Active derivates of acids for formula (V) include for example acid anhydrides or acid halides such as acid chlorides as outlined earlier.

Amino acids and their dervatives as depicted by general formulae (V) and (VI) can be obtained in chiral or racemic form. In the chiral form they provide asymmetric building blocks for the chiral synthesis of compounds of general formula (1). Many of these derivatives can be readily obtained from commercially available starting materials using methods known to those skilled in the art. (See "The Practice of Peptide Synthesis" by M. Bodanszk et al, Springer Verlag, New York, 1984, P. L. Durette, WO92/21360).

As a further extension to the present invention compounds of general formula (II) may be prepared by nucleophilic substitution of compounds of general formula (VII)

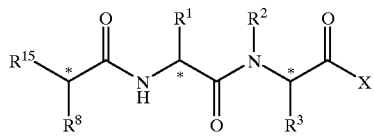

(VII)

wherein $R^{15}$ represents a suitable leaving group (e.g. a halogen such as bromide, or an alkylsulphonate ester such as methansulphonate) with a thiol of general formula (VIII)

$R^7SH$ (VIII)

Wherein $R^7$ represents a suitable protecting group (eg. tert-butyl or acetate), using standard conditions known to those skilled in the art as exemplified in WO 90/05719. Thiols of general formula (VIII) may be obtained from commercially available starting materials using methods known to those skilled in the art. Many thiols of general formula (VIII) are also commercially available.

Compounds of general formula (VII) may be prepared by coupling an acid of general formula (IX)

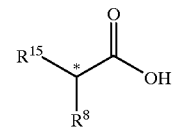

(IX)

wherein $R^{15}$ and $R^8$ are as defined above (or suitably protected versions thereof) or an active derivative thereof, with an amine of formula (IV) using similar coupling conditions to those described for the preparation of compounds of formula (II). Carboxylic acids of the structure depicted in formulae (III) and (IX) can be obtained in chiral or racemic form. Many of these derivatives can be readily obtained from commercially available starting materials using methods known to those skilled in the art (see WO 90/05719).

As a further extension to the present invention, intermediates of general formula (II) may be prepared by coupling an acid of formula (X)

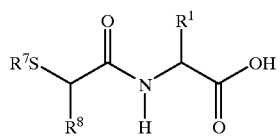

wherein $R^1$, $R^7$ and $R^8$ are as defined above, or an active derivative thereof, with an amine of formula (VI) by the procedure described previously.

Acids of general formula (X) may in turn be preapred by coupling an acid of formula (III), or an active derivative thereof with an amine of formula (VI), where X=OH or a suitably protected derivative therof followed by removal of any protecting groups.

Active derivates of acids for formula (V) include for example acid anhydrides or acid halides such as acid chlorides as outlined earlier.

Compounds of formula (I) may also be prepared by interconversion of other compounds of formula (I). Thus, for example, a compound of formula (I) wherein $R^1$ is a $C_{1-6}$ alkyl group may be prepared by hydrogenation (using palladium on carbon in suitable solvent, such as an alcohol—eg ethanol) of a compound of formula (I) wherein $R^1$ is a $C_{2-6}$ alkenyl group. A further example would include a compound of formula (I) wherein $R^7$ is a group $R^{10}$ CO may be prepared by acylation (using a suitable acid chloride $R^{10}$ COCl, in the presence of a base such as a triethylamine in a suitable solvent, such as a chlorinated solvent—eg dichloromethane) of a compound of formula (I) wherein $R^7$ is H.

Any mixtures of final products or intermediates obtained can be separated on the basis of the pysico-chemical differences of the constituents, in known manner, into the pure final products or intermediates, for example by chromatography, distillation, fractional crystallization, or by formation of a salt if appropriate or possible under the circumstances.

The compounds according to the invention exhibit in vitro inhibiting activities with respect to stromelysin, collagenase and gelatinase. Compounds according to the invention also exhibit in vitro inhibition of TNFα release. The activity and selectivity of the compounds may be determined by use of the appropriate enzyme inhibition test, for example as described in Example A hereinafter.

This invention also relates to a method of treatment for patients (including man and/or mammalian animals raised in the dairy, meat or fur industries or as pets) suffering from disorders or diseases which can be attributed to matrix metalloproteinases and/or TNFα as previously described, and more specifically, a method of treatment involving the administration of the matrix metalloproteinase inhibitors of formula (I) as the active constituents.

Accordingly, the compounds of formula (I) can be used among other things in the treatment of osteoarthritis and rheumatoid arthritis, and in diseases and indications resulting from the over-expression of these matrix metalloproteinases such as found in certain metastatic tumour cell lines.

As mentioned above, compounds of formula (I) are useful in human or veterinary medicine since they are active as inhibitors of TNFα and MMPs. Accordingly in another aspect, this invention concerns:

a method of management (by which is meant treatment or prophylaxis) of disease or conditions mediated by TNFα and/or MMPs in mammals, in particular in humans, which method comprises administering to the mammal an effective amount of a compound of formula (I) above, or a pharmaecutically acceptable salt thereof; and a compound of formula (I) for use in human or veterinary medicine, particularly in the management (by which is meant treatment or prophylaxis) of diseases or conditions mediated by TNFα and/or MMPs; and the use of a compound of formula (I) in the preparation of an agent for the management (by which is meant treatment or prophylaxis) of diseases or conditions mediated by TNFα and/or MMPs.

The disease or conditions referred to above include inflammation, fever, cardiovascular effects, haemorrhage, coagulation and acute phase response, cachexia and anorexia, acute infections, shock states, graft versus host reactions and autoimmune disease; and those involving tissue breakdown such as bone resportion, inflammatory diseases, dermatological conditions, tumour growth, angiogenesis and invasion by secondary metastases, in particular rheumatoid arthritis, osteoarthritis, periodontitis, gingivitis, corneal ulceration, tumour growth, angiogenesis and invasion by secondary metastases.

For the treatment of rheumatoid arthritis, osteoarthritis, and in diseases and indications resulting from the over-expression of matrix metalloendoproteinases such as found in certain metastatic tumour cell lines or other diseases mediated by the matrix metalloendoproteinases or increased TNFα production, the compounds of formula (I) may be administered orally, topically, parenterally, by inhalation spray or rectally in dosage unit formulations containing non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats etc, the compounds of the invention are effective in the treatment of humans.

The pharmaceutical composition containing the active ingredient may be in a form suitable for oral use, for example, as tablets, troches, lozenges, aqueous or oily suspension, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaecutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastointestinal tract and thereby provide a sustained action over a longer period. For example, a time delay material such as glyceryl monostearate or glyeryl distearate may be employed. They may also be coated by the techniques described in the U.S. Pat. Nos. 4,256,108; 4,166,452; and 4,265,874 to form osomotic therapeutic tablets for control release.

Formulations for oral use may also be presented as hard gelatin capsules where in the active ingredient is mixed with an inert solid diluent, for example calcium carbonate, calcium phosphate or kaolin, or as solft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methycellulose, hydroxypropylmethylcellulose, sodium alginate, polyvinyl-pyrrolidone, gum tragacanth and gum acacia; dispersing or wetting agents may be a naturally occuring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such a polyoxyethylene with partial esters derived from fatty acids and hexitol anhydrides, for example polyoxyethylene sorbitan monooleate. The aqueous suspension may also contain one or more preservatives, for example ethyl, or n-propyl, p-hyroxybenzoate, one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified, for example sweetening, flavouring and colouring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occuring gums, for example gum acacia or gum tragancanth, naturally-occuring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavouring agents.

Syrups and elixirs may be formulated with sweetening agents, for example gycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be in a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc containing the compounds of Formula (I) are employed. (For purposes of this application, topical application shall include mouth washes and gargles.)

Dosage levels of the order of from about 0.05 mg to about 140 mg per kilogram of body weight per day are useful in the treatment of the above-indicated conditions (about 2.5 mg to about 7 gms per patient per day). For example, inflammation may be effectively treated by the administration of from about 0.01 to 50 mg of the compound per kilogram of body weight per day (about 0.5 mg to about 3.5 gms per patient per day).

The amount of active ingredient that may be combined with the carrier materials to produce a single dosage form will vary depending upon the host treated and the particular mode of administration. For example, a formulation intended for the oral administration of humans may vary from about 5 to about 95 percent of the total composition. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet time of administration, route of administration, rate of excretion, drug combination and the severity of the particular disease undergoing therapy.

The following Examples 1 to 79 illustrate the invention and their preparation (via the green Intermediates, as appropriate). Examples A to G illustrate test procedures.

In the Examples, the following abbreviations are used:
RT Room temperature
DCC Dicyclohexylcarbodiimide
EDC 1-(3-Dimethylaminopropyl)-3-ethyl carbodiimide hydrochloride
$TNF_\alpha$ Tumour necrosis factor $\alpha$
PMA Phorbol-13-myristate-12-acetate
ELISA Enzyme linked immunosorbent assay

INTERMEDIATE 1

(RS)-2-Bromo-4-methoxycarbonylbutanoic Acid

A solution of d-methyl-D,L-glutamic acid (6.0 g) (preparation according to Hanby et al, J. Chem. Soc. (1950), 51:3239) and potassium bromide (15.5 g) in aqueous sulfuric acid (1.25 M, 100 ml) was treated at 0° C. portionwise with sodium nitrite (4.0 g) over 1 h. The solution was allowed to warm to RT and was stirred over 2 h, then extracted with ethyl acetate (2×100 ml). The combined extracts were dried ($MgSO_4$) and evaporated in vacuo to give the title compound as a colourless oil (4.5 g).

TLC $R_f$ 0.14 (25% EtOAc-hexanes)

Similarly prepared were:

INTERMEDIATE 2

(RS)-2-Bromo-5-methoxycarbonylpentanoic Acid

From (RS)-2-amino-5-methoxycarbonylpentanoic acid (1.8 g) (preparation based on the esterification procedure of Hanby et al, J. Chem. Soc. (1950), 51:3239) as a pale brown oil (1.95 g).

TLC $R_f$ 0.30 (5% MeOH-$CH_2Cl_2$)

INTERMEDIATE 3

(RS)-2-Bromo-6-methoxycarbonylhexanoic Acid

From (RS)-2-amino-6-methoxycarbonylhexanoic acid (3.93 g) (preparation based on the esterification procedure of Hanby et al, J. Chem. Soc. (1950), 51:3239) as a colourless oil (4.39 g).

TLC $R_f$ 0.26 (5% MeOH-$CH_2Cl_2$)

INTERMEDIATE 4

(RS)-2-Acetylmercapto-3-methoxycarbonylpropionic Acid

A solution of potassium thiolacetate (1.48 g) in methanol (2 ml) was added to a solution of mono-methylmaleate (1.64 g) (prepared according the procedure exemplified in J. Am. Chem. Soc. (1986), 108:3) and the mixture was stirred overnight at RT. The solvent was removed by evaporation and the residue was partitioned between water (30 ml) and dichloromethane (30 ml), and the aqueous layer was then acidified to pH3 with 2N aqueous hydrochloric acid. The layers were separated and the aqueous layer was extracted with dichloromethane (2×30 ml). The combined organic extracts were dried ($MgSO_4$) and evaporated in vacuo to give a brown oil. Purification by flash column chromatography (eluting with 10% methanol in dichloromethane) gave the title compound as a colourless oil (0.48 g).

TLC $R_f$ 0.30 (10% $MeOH-CH_2Cl_2$)

INTERMEDIATE 5

(RS)-2-Acetylmercapto-4-methoxycarbonylbutanoic Acid

Potassium thiolacelate (2.0 g) was added to a solution of intermediate 1 (3.0 g) in ethanol (30 ml) and the mixture was stirred at RT overnight. The solution was evaporated in vacuo and the residue was partitioned between ethyl acetate (30 ml) and water (30 ml). The organic layer was then washed with saturated brine (30 ml), dried ($MgSO_4$) and evaporated in vacuo to give the title compound as a colourless oil (1.83 g).

TLC $R_f$ 0.46 (EtOAc)

Similarly prepared were:

INTERMEDIATE 6

(RS)-2-Acetylmercapto-5-methoxycarbonylpentanoic Acid

From Intermediate 2 (1.89 g) as a yellow oil (0.87 g).
TLC $R_f$ 0.30 (5% $MeOH-CH_2Cl_2$)

INTERMEDIATE 7

(RS)-2-Acetylmercapto-6-methoxycarbonylhexanoic Acid

From Intermediate 3 (4.3 g) as a yellow oil (2.78 g).
TLC $R_f$ 0.23 (5% $MeOH-CH_2Cl_2$)

INTERMEDIATE 8

(RS)-(1,1-Dimethylethyl) 2,4-dibromobutyrate

Bromine (31.3 ml, 0.54 mol) was added dropwise over 4h at 100° C. to neat stirring 4-bromobutyryl chloride (100 g, 0.54 mol). The resulting acid chloride was cooled then added dropwise at 0° C. to a stirred solution of tert-butanol (240 ml) and triethylamine (64 ml, 0,461 mol) in anhydrous dichloromethane (600 ml). 2M Hydrochloric acid was added and the layers separated. The organic portion was then washed sequentially with 10% sodium metabisulphite solution (2×500 ml), water (500 ml) and brine (500 ml), dried ($MgSO_4$) and evaporated in vacuo to provide the title compound (120 g, 86%) as a brown liquid.

$^1$H NMR (250 MHz; $CDCl_3$), Ref., TMS) 1.50 (9H, s), 2.45 (2H, q), 3.55 (2H, t) and 4.40 (1H, dd).

Similarly prepared were:

INTERMEDIATE 9

(RS)-(1,1-Dimethylethyl) 2,5-dibromopentanoate

From 5-bromovaleryl chloride (75 g, 0.37 mol), as a brown oil (81 g, 68%).

$^1$H NMR (250 MHz; $CDCl_3$), Ref., TMS) 1.50 (9H, s), 1.8–2.3 (4H,m), 3.45 (2H, t) and 4.18 (1H, dd).

INTERMEDIATE 10

(RS)-(1,1-Dimethylethyl) 2,6-dibromohexanoate

From 6-bromohexanoyl chloride (100 g, 0.47 mol), as a brown oil (133 g, 87%).

$^1$H NMR (250 MHz; $CDCl_3$, Ref., TMS) 1.50 (9H, s), 1.6–2.1 (6H, m), 3.4 (2H, t) and 4.1 (1H, dd).

INTERMEDIATE 11

(RS)-(1,1-Dimethylethyl) 2,4-bis-(acetylmercapto)butyrate

Potassium thiolacetate (1.51 g, 13.2 mmol) was added to a stirred solution of intermediate 8 (2 g, 6.6 mmol) in methanol (25 ml) and the mixture stirred at RT overnight. The mixture was diluted with dichloromethane (100 ml), washed with brine (2×50 ml), dried ($MgSO_4$) and evaporated in vacuo to a yellow oil. Purification by flash column chromatography (eluting with 30% dichloromethane in hexane) provided the title compound (1.1 g, 57%) as a colourless oil.

TLC $R_f$ 0.57 ($CH_2Cl_2$)

Similarly prepared were:

INTERMEDIATE 12

(RS)-(1,1-Dimethylethyl) 2,5-bis-(acetylmercapto)pentanoate

From intermediate 9 (2 g, 6.32 mmol), as a colourless oil (1.12 g, 57%)

TLC $R_f$ 0.57 ($CH_2Cl_2$)

INTERMEDIATE 13

(RS)-(1,1-Dimethylethyl) 2,6-bis-(acetylmercapto)hexanoate

From intermediate 10 (2 g, 6.32 mmol), as a colourless oil (1.09 g, 57%)

TLC $R_f$ 0.57 ($CH_2Cl_2$)

INTERMEDIATE 14

(RS)-2,3-Bis-(acetylmercapto)propionic Acid

A solution of thiolacetic acid (1.12 g) in 1N aqueous potassium hyroxide (14.7 ml) was added dropwise to a solution of 2,3-dibromopropionic acid (1.71 g) in 1N aqueous potassium hydroxide (7.35 ml) and the mixture was stirred 5 h at RT. The pH of the mixture was adjusted to 8–9 by the addition of further 1N aqueous potassium hydroxide and the mixture was stirred a further 2 h, then acidified to pH1–2 by the addition of concentrated hydrochloric acid and extracted with ethyl acetate (2×25 ml). The combined extracts were dried (Na$_2$SO$_4$) and evaporated to give a yellow oil. The product from two reactions was combined and purification by flash column chromatography (eluting with 4% acetic acid-toluene) gave the title compound as a colourless oil (0.422 g).

TLC R$_f$ 0.15 (5% AcOH-toluene)

INTERMEDIATE 15

(RS)-2,4-Bis-(acetylmercapto)butyric Acid

A solution of intermediate 11 (1.1 g, 3.7 mmol) in dichloromethane (50 ml) was treated with trifluoroacetic acid (2.9 ml, 37 mmol) and the mixture stirred at RT overnight. Water (50 ml) was added and the mixture extracted with dichloromethane (3×40 ml). The combined organic extracts were then washed with water (50 ml) and brine (50 ml), dried (MgSO$_4$) and evaporated in vacuo to provide the product (870 mg, 98%) as a pale yellow oil.

TLC R$_f$ 0.12 (25% MeOH-CH$_2$Cl$_2$)

Similarly prepared were:

INTERMEDIATE 16

(RS)-2,5-Bis-(acetylmercapto)pentanoic Acid

From intermediate 12 (1.1 g 3.6 mmol), as a pale yellow oil (906 mg, 100%)

TLC R$_f$ 0.12 (25% MeOH-CH$_2$Cl$_2$)

INTERMEDIATE 17

(RS)-2,6-Bis-(acetylmercapto)hexanoic Acid

From intermediate 13 (1.1 g, 3.6 mmol), as a pale yellow oil (895 mg, 98%)

TLC R$_f$ 0.12 (25% MeOH-CH$_2$Cl$_2$)

INTERMEDIATE 18

4-Phthalimidobutanoic Acid

N-Carboethoxyphthalimide (10.96 g) was added on one portion to a vigorously stirred solution of 4-aminobutanoic acid (5.16 g) and sodium carbonate (5.35 g) in water (150 ml) at RT. The mixture was stirred until essentially all the solid material had dissolved (30 min), then it was filtered. The filtrate was acidified to pH1 with 6N aqueous hydrochloric acid (ca. 22 ml) and the white precipitate was collected by filtration and washed thoroughly with water (150 ml). The solid was dried in air, then in vacuo to give the title compound as a colourless solid (7.35 g).

$^1$H NMR (250 MHz; CDCl$_3$, Ref., TMS) d 2.03 (2H. pent.) 2.42 (2H, t) 3.78 (2H, t), 7.65–7.77 (2H, m), 7.81–7.90 (2H, m)

Similarly prepared were:

INTERMEDIATE 19

5-Phthalimidopentanoic acid

From 5-aminopentanoic acid (5.0 g) as a colourless solid (6.8 g).

$^1$H NMR (250 MHz; CDCl$_3$, Ref., TMS) d 1.6–1.8 (4H, m) 2.20 (2H, t) 3.85 (2H, t), 7.70–7.75 (2H, m), 7.85–7.95 (2H, m), 10.2 (1H, br s)

INTERMEDIATE 20

6-Phthalimidohexonoic acid

From 6-aminohexanoic acid (5.0 g) as a colourless solid (5.8 g).

$^1$H NMR (60 MHz; CDCl$_3$, Ref., TMS) 1.5–2.4 (6H, m) 2.3 (2H, t) 3.80 (2H, t), 7.8–8.1 (4H, m), 10.4 (1H, br s)

INTERMEDIATE 21

2-(3-Phthalimidophenyl)acetic acid

From 2-(3-aminophenyl)acetic acid (3.0 g) as an off-white solid (4.0 g, 72%).

TLC R$_f$ 0.36 (7.5% MeOH-0.5% AcOH—CH$_2$Cl$_2$)

INTERMEDIATE 22

Cis-3-Aminocyclopent-4,5-enecarboxylic acid

A solution of racemic lactam (50 g, 0.458 mol) in 2N hydrochloric acid (1000 ml) was heated under reflux for 1 h. The mixture was evaporated in vacuo and the residue crystallised from acetone to provide the hydrochloride salt of the title compound (73 g, 97%) as a white solid.

This hydrochloride salt (20 g, 0.122 mol) was dissolved in water (300 ml) and the stirred solution treated with amberlite (IRA-67) ion exchange resin until pH 7 was reached. The resin was then removed by filtration, the solvent removed in vacuo and the residue crystallised from acetone to provide the title compound (13.7 g, 88%) as a white solid.

INTERMEDIATE 23

CIS-3-Phthalimidocyclopent-4,5-enecarboxylic acid

From intermediate 22 hydrochloride (22.3 g, 0.136 mol), as a white solid (13.7 g, 39%).

TLC R$_f$ 0.37 (1% AcOH-5% MeOH—CH$_2$Cl$_2$)

INTERMEDIATE 24

Trans-Methyl 3-Phthalimidocyclopent-4,5-enecarboxylate

Intermediate 23 (23.2 g, 0.183 mol) and phthalic anhydride (27.03 g, 0.183 mol) were powdered together and melted at 190° C. under nitrogen with stirring. The mixture was allowed to cool to RT and the residue treated with ethyl acetate (120 ml). Activated charcoal (1.0 g) was added and the mixture heated under reflux for 30 min, filtered through celite and the filtrate evaporated in vacuo to provide the intermediate phthalimido-acid, a 1:1 mixture of cis/trans isomers, as a pale yellow solid (45.7 g, 97%).

A solution of this acid in methanol (300 ml) was treated with conc. hydrochloric acid (0.5 ml) and the mixture heated under reflux for 30 min, allowed to cool to RT and the solvent evaporated in vacuo. The residue was dissolved in ethyl acetate (400 ml) and the solution washed with 8% sodium bicarbonate (2×100 ml), water (100 ml) and brine (100 ml), dried (MgSO$_4$) and evaporated in vacuo to provide the phthalimodoester as a 1:1 mixture of cis/trans isomers. Separation by flash column chromatography (eluting with 60% ether-pentane) provided the title compound (9.72 g, 20%) as a white solid.

TLC R$_f$ 0.46 (40% pentane-ether)

INTERMEDIATE 25

Trans-3-Phthalimidocyclopent-4,5-enecarboxylic acid

A solution of intermediate 24 (9.72 g, 35.8 mmol) in a mixture of 0.5N hydrochloric acid (100 ml) and glacial acetic acid (100 ml) was heated under reflux for 30 min. The mixture was diluted with water (200 ml) and extracted with ethyl acetate (3×100 ml). The combined extracts were washed with brine (100 ml), dried (MgSO$_4$) and evaporated in vacuo to provide the crude product which was crystallised from ether (7.56 g, 82%) as a white solid.

TLC R$_f$ 0.48 (1% AcOH-5% MeOH—CH$_2$Cl$_2$)

INTERMEDIATE 26

Cis-3-Phthalimidocyclopentanecarboxylic acid

Intermediate 23 (15.1 g, 58.7 mmol) was hydrogenated at RT and atmospheric pressure over 5% palladium on charcoal (2 g) in ethyl acetate (700 ml) overnight. The catalyst was removed by filtration through celite and the filtrate evaporated in vacuo to provide the title compound (15 g, 98%) as white solid.

TLC $R_f$ 0.37 (1% AcOH-5% MeOH—$CH_2Cl_2$)

Similarly prepared was:

INTERMEDIATE 27

Trans-3-Phthalimidocyclopentanecarboxylic acid

From intermediate 25 (7.55 g, 29.3 mmol), as a white solid (7.04 g, 93%)

TLC $R_f$ 0.47 (1% AcOH-5% MeOH—$CH_2Cl_2$)

INTERMEDIATE 28

Cis-(1,1-Dimethylethyl(3-Phthalimidocyclopentylacetate

A solution of intermediate 26 (5.09 g, 19.06 mmol) in dry dichloromethane (60 ml) was treated with oxalyl chloride (3.4 ml, 39.3 mmol) then dimethylformamide (1 drop). The mixture was stirred at RT for 2 h then the solvent evaporated in vacuo to provide the intermediate acid chloride.

The residue was dissolve in tetrahydrofuran (30 ml) then treated with a solution of diazomethane in ether (200 ml, ca. 80 mmol) at 0° C. The mixture was stirred at RT overnight then evaporated in vacuo to provide the diazoketone as a yellow solid. The diazoketone was dissolved in tert-butanol (100 ml) and heated under reflux while a solution of silver benzoate (438 mg, 1.9 mmol) in triethylamine (5 ml) was added in small portions over 2 h. The mixture was heated under reflux for a further 1 h then cooled to RT, filtered through celite and the filtrate evaporated in vacuo to provide a yellow solid. The residue was dissolved in dichloromethane (75 ml) and the solution washed sequentially with 8% sodium bicarbonate (50 ml), water (50 ml) and brine, dried ($MgSO_4$) and evaporated in vacuo to provide the crude product. Purification by flash column chromatography (eluting with 50% ether-pentane) provided the title compound (3.8 g, 60%) as a white solid.

TLC $R_f$ 0.52 (50% pentane-ether)

Similarly prepared was:

INTERMEDIATE 29

Trans-1,1-Dimethylethyl) 3-Phthalimidocyclopentylacetate

From intermediate 27 (1.41 g, 5.44 mmol), as a white solid (1.22 g, 70%).

TLC $R_f$ 0.58 (50% pentane-ether)

INTERMEDIATE 30

Cis-3-Phthalimidocyclopentylacetic acid

A solution of intermediate 28 (1.78 g, 5.4 mmol) in dichloromethane (20 ml) was treated with trifluoracetic acid (2.1 ml, 27 mmol) and the mixture stirred at RT overnight. The solvent and excess trifluoracetic acid was removed in vacuo to provide the title compound (1.41 g, 96%) as a white solid.

TLC $R_f$ 0.32 (30% pentane-ether)

Similarly prepared was:

INTERMEDIATE 31

Trans-3-Phthalimidocyclopentylacetic acid

From intermediate 29 (1.18 g, 3.58 mmol), as a white solid (842 mg, 86%).

TLC $R_f$ 0.41 (30% pentane-ether)

INTERMEDIATE 32

(RS)2-Bromo-5phthalimidopentanoic acid

Intermediate 19 (5.0 g 20.2 mmol) and thionyl chloride (10 ml) were heated together at 65° C. for 30 min. N-Bromosuccinimide (5.4 g) and further thionyl chloride were added, plus 48% aqueous HBr (1 drop). The solution was heated at 60° C. for 10 min then 70° C. for 2 h 15 min. Further N-bromosuccinimide (850 mg) was added and the mixture was heated at 70° C. for 2 h. Excess thionyl chloride was removed by evaporation under reduced pressure and the oily residue was diluted with dry tetrahydrofuran (200 ml) and water (200 ml). The mixture was then treated cautiously with solid sodium bicarbonate to pH 7–8 then stirred overnight at RT. Excess tetrahydrofuran was removed in vacuo and the residue washed with dichloromethane (3×300 ml). The aqueous portion was then cautiously acidified to pH 1 using 6M hydrochloric acid and extracted with dichloromethane (4×200 ml). The combined extracts were then washed with water (2×400 ml) and brine (400 ml), dried ($MgSO_4$) and evaporated in vacuo to provide the product (4.7 g, 71%) as a fawn solid.

TLC $R_f$ 0.47 (EtOAc)

Similarly prepared were:

INTERMEDIATE 33

(RS) 2-Bromo-20(3-phthalimidophenyl)acetic acid

From intermediate 21 as a colourless solid (588 mg, 75%)

TLC $R_f$ 0.19 (5% MeOH-0.1% AcOH—$CH_2Cl_2$)

INTERMEDIATE 34

Cis-a-Bromo-3-phthalimidocyclopentylacetic acid

From intermediate 30 (1.41 g, 5.16 mmol), as a buff foam (1.59 g, 87%).

TLC $R_f$ 0.46 (2% MeOH-ether)

INTERMEDIATE 35

Trans-a-Bromo-3-phthalimidocyclopentylacetic acid

From intermediate 31 (815 mg, 2.98 mmol), as a yellow-brown foam (805 mg, 77%)

TLC $R_f$ 0.48 (2% MeOH-ether)

INTERMEDIATE 36

(RS)2-Acetylmetcapto-5-phthalimidopentanoic acid

A solution of intermediate 33 (3.0 g, 9.2 mmol) in methanol (30 ml) was treated with potassium thiolacetate (1.05 g, 9.2 mmol) and the mixture stirred at RT overnight. The mixture was evaporated in vacuo, the residue dissolved in dichloromethane (100 ml) then the solution washed with water (2×50 ml), dried ($MgSO_4$) and evaporated in vacuo to provide the product (2.4 g, 81%) as a pale yellow foam.

TLC $R_f$ 0.43 (EtOAc)

Similarly prepared were:

INTERMEDIATE 37

(RS) 2-Acetylmercapto-2-(3phthalimido)phenylacetic acid

From intermediate 33 as a colourless solid (722 mg, 100%)

TLC $R_f$ 0.15 (5% MeOH-0.1% AcOH—$CH_2Cl_2$)

INTERMEDIATE 38

CIS-a-(Acetylmercapto)-3-phthalimidocyclopentylacetic acid

From intermediate 34 (2.01 g, 5.71 mmol), as a brown foam (1.44 g, 73%)

TLC $R_f$ 0.42 (Ether)

INTERMEDIATE 39

Trans-a-(Acetylmercapto)-3-phthalimidocyclopentylacetic acid

From intermediate 35 (774 mg, 2.2 mmol), as a beige foam (329 mg, 43%)

TLC $R_f$ 0.45 (Ether)

INTERMEDIATE 40

(RS)-N-[2-Bromo-4phthalimidobutanoyl]-L-leucyl-L-phenylanlanine N-methyl amide

Intermediate 18 (2.33 g) and thionyl chloride (2.92 ml) were heated together at 65° C. for 30 min. N-Bromosuccinimide (2.51 g) and further thionyl chloride were added, plus 48% aqueous HBr (1 drop). The solution was heated at 60° C. for 10 min then 70° C. for 2 h 15 min. Further N-bromosuccinimide (850 mg) was added and the mixture was heated at 70° C. for 2 h. Excess thionyl chloride was removed by evaporation under reduced pressure and the oily residue was diluted with dry dichloromethane (10 ml). A portion of the supernatant (4.0 ml) was added to a solution of L-leucyl-L-phenylanlanine N-methyl amide (500 mg) and triethylamine (0.24 ml) in dry dichloromethane (10 ml) at 0° C., and this mixture was stirred overnight at RT. The mixture was diluted with dichloromethane and washed with saturated aqueous sodium bicarbonate solution (50 ml), 1N aqueous hydrochloric acid (50 ml), and saturated brine (50 ml), then dried ($MgSO_4$) and evaporated in vacuo to give a brown solid. This material was purified by flash column chromatography (4×18 cm; eluting with 2% methanol-dichloromethane) to give the title compound as an off-white solid (530 mg).

TLC $R_f$ 0.44 (5% MeOH—$CH_2Cl_2$)

Similarly prepared were:

INTERMEDIATE 41
(RS)-N-[2-Bromo-5-phthalimidopentanoyl]-L-leucyl-L-phenylanlanine N-methyl amide From Intermediate 19 (4.0 g) and L-leucyl-L-phenylalanine N-methyl amide (1.18 g), as a pink solid (1.2 g).

TLC $R_f$ 0.34 (5% MeOH—$CH_2Cl_2$)

INTERMEDIATE 42
(RS)-N-[2-Bromo-6phthalimidohexanyol]-L-leucyl-L-phenylalanine N-methyl amide From Intermediate 20 (4.0 g) and L-leucyl-L-phenylalanine N-methyl amide (1.18 g), as a near colourless solid (1.0 g).

TLC $R_f$ 0.52 (10% MeOH—$CH_2Cl_2$)

INTERMEDIATE 43
(RS)-2-[(1,1-Dimethylethyl)mercapto]-5-phthalimidopentanoic acid Tert-butylthiol (11.3 ml, 0.1 mol) was added to a stirred solution of potassium tert-butoxide (22.45 g, 0.1 mol) in anhydrous tetrahydrofuran (215 ml) and the mixture stirred at RT for 20 min. A solution of intermediate 13 (32.6 g, 0.1 mol) in anhydrous tetrahydrofuran (80 ml) was then added and the mixture stirred at RT overnight. Water (300 ml) was added, the mixture acidified to pH 1 with 1N hydrochloric acid and extracted with dichloromethane (3×200 ml). The combined extracts were then dried ($MgSO_4$) and evaporated in vacuo to provide a yellow oil. Purification by flash column chromatography (eluting with 5–15% dichloromethane in ethyl acetate) then crystallisation from dichloromethane/hexane furnished the title compound (22 g, 66%) as a pale yellow solid.

TLC $R_f$ 0.48 (10% MeOH—$CH_2Cl_2$)

INTERMEDIATE 44
(RS)-N-[2-[(1,1-Dimethylethyl)mercapto]-5-phthalimidopentanoyl]-L-leucyl-L-phenylalanine N-methyl amide A solution of intermediate 43 (8.06 g., 24 mmol) and L-leucyl-L-phenylalanine N-methyl amide (7.0 g, 24 mmol) in dichloromethane (250 ml) was treated with N-hydroxybenzotriazole (3.9 g, 28.9 mmol) then EDC (5.06 g, 26.4 mmol) and the mixture stirred at RT overnight. The mixture was washed with 1N hydrochloric acid (300 ml) and the aqueous portion re-extracted with dichloromethane (2×100 ml). The combined extracts were washed sequentially with 1N hydrochloric acid (300 ml), 8% sodium bicarbonate (300 ml), water (300 ml) and brine (300 ml), dried ($MgSO_4$) and evaporated in vacuo to provide a pale yellow solid. Purification by flash column chromatography (eluting with 5% methanol in dichloromethane) provided the title compound (12.8 g, 88% as a near white solid.

TLC $R_f$ 0.55 (10% MeOH—$CH_2Cl_2$)

INTERMEDIATE 45
(RS)-N-[2-[(1,1Dimethylethyl)mercapto]-5-aminopentanoyl]-L-leucyl-L-phenylalanine N-methyl amide A solution of intermediate 44 (2.56 g, 4.2 mmol) in a mixture of tetrahydrofuran (10 ml) and ethanol (50 ml) was treated with hydrazine hydrate (10 ml, xs) and the mixture heated under reflux for 2 h. After cooling to RT water (30 ml) was added, the solvent removed in vacuo, the residue acidified to pH 1 with 1N hydrochloric acid and washed with dichloromethane (2×100 ml). The aqueous layer was then basified to pH 14 with 2M sodium hydroxide and extracted with dichloromethane (2×100 ml). The combined extracts were washed with brine (100 ml), dried ($MgSO_4$) and evaporated in vacuo to provide a pale yellow solid. Purification by flash column chromatography (eluting with 10–25% methanol in dichloromethane) provided the title compound (9.2 g, 91%) as a near white solid.

TLC $R_f$ 0.23 (30% MeOH—$CH_2Cl_2$)

INTERMEDIATE 46
(RS)-N-[2-[(1,1-Dimethylethyl)mercapto]-5-(acetylamino) pentanoyl]-L-leucyl-L-phenylalanine N-methyl amide Acetyl chloride (0.5 ml, 7 mmol) was added to a stirred solution of intermediate 45 (1.14 g, 2.38 mmol) and triethylamine (2 ml, 14.4 mmol) in anhydrous dichloromethane (45 ml), the mixture was then stirred at RT overnight. The mixture was diluted with dichloromethane (75 ml) and washed successively with 1N hydrochloric acid (100 ml), 8% sodium bicarbonate (100 ml), water (100 ml), dried (MgSO) and evaporated in vacuo to provide a pale yellow solid. Purification by flash column chromatography (eluting with 5% methanol in dichloromethane) provided the title compound (1.2 g, 95%) as a near white solid.

TLC $R_f$ 0.31 (10% MeOH—$CH_2Cl_2$)

Similarly prepared were:

INTERMEDIATE 47
(RS)-N-[2-[(1,1-Dimethylethyl)mercapto]-5-(benzoylamino)pentanoyl]-L-leucyl-L-phenylalanine N-methyl amide From intermediate 45 (2.86 g, 5.97 mmol) and benzoyl chloride (0.84 ml, 7.2 mmol), as a near white solid (3.43 g, 99%).

TLC $R_f$ 0.41 (10% MeOH—$CH_2Cl_2$)

INTERMEDIATE 48
(RS)-N-[2-[(1,1,-Dimethylethyl)mercapto]-5-succinimidopentanoyl]-L-leucyl-L-phenylalanine N-methyl amide From intermediate 45 (1.14 g, 2.38 mmol) and succinic anhydride (0.33 ml, 3.3 mmol), as a near white solid (0.54 g, 40%).

TLC $R_f$ 0.58 (10% MeOH—$CH_2Cl_2$)

INTERMEDIATE 49
(RS)-N-[2-[(1,1-Dimethylethyl)mercapto]-5-(methanesulphonyl) aminopentanoyl]-L-leucyl-L-phenylalanine N-methyl amide From intermediate 45 (2.03 g, 4.24 mmol) and methanesulphonyl chloride (0.35 ml, 4.6 mmol), as a near white solid (1.78 g, 77%).

TLC $R_f$ 0.46 (10% MeOH—$CH_2Cl_2$)

INTERMEDIATE 50
(RS)-N-[2-[(1,1-Dimethylethyl)mercapto]-5-(benzenesulphonyl) aminopentanoyl]-L-leucyl-L-phenylalanine N-methyl amide From intermediate 45 (2.03 g, 4.24 mmol) and benzenesulphonyl chloride (0.59 ml, 4.6 mmol), as a near white solid (2.18 g, 85%).

TLC $R_f$ 0.54 (10% MeOH—CH$_2$Cl$_2$)

INTERMEDIATE 51
(RS)-N-[2-[(1,1-Dimethylethyl)mercapto]-5-methoxycarbonyl) aminopentanoyl]-L-leucyl-L-phenylalanine N-methyl amide From intermediate 45 (200 mg, 0.43 mmol) and methyl chloroformate (0.03 ml, 0.41 mmol), as a near white solid (196 mg, 89%).

TLC $R_f$ 0.32 (5% MeOH—CH$_2$Cl$_2$)

INTERMEDIATE 52
(RS)-N-[2-[(1,1-Dimethylethyl)mercapto]-5-(benzyloxycarbonyl)aminopentanoyl]-L-leucyl-L-phenylalanine N-methyl amide From intermediate 45 (200 mg, 0.43 mmol) and benzyl chloroformate (0.06 ml, 0.41 mmol), as a near white solid (230 mg, 93%).

TLC $R_f$ 0.44 (5% MeOH—CH$_2$Cl$_2$)

INTERMEDIATE 53
(RS)-N-[2-[(1,1-Dimethylethyl)mercapto]-5-(4-pyridylcarbonyl) aminopentanoyl]-L-leucyl-L-phenylalanine N-methyl amide From intermediate 45 (2.03 g, 4.24 mmol) and isonicotinoyl chloride (834 mg, 4.66 mmol), as a near white solid (1.81 g, 77%).

TLC $R_f$ 0.22 (10% MeOH—CH$_2$Cl$_2$)

INTERMEDIATE 54
(RS)-N-[2-[(1,1-Dimethylethyl)mercapto]-5-(3-pyridylcarbonyl) aminopentanoyl]-L-leucyl-L-phenylalanine N-methyl amide From intermediate 45 (200 mg, 0.42 mmol) and nicotinoyl chloride (83 mg, 0.47 mmol), as a near white solid (130 mg, 56%).

TLC $R_f$ 0.26 (10% MeOH—CH$_2$Cl$_2$)

INTERMEDIATE 55
(RS)-N-[2-[(1,1-Dimethylethyl)mercapto]-5-(2-pyridylcarbonyl) aminopentanoyl]-L-leucyl-L-phenylalanine N-methyl amide From intermediate 45 (200 mg, 0.42 mmol) and picolinoyl chloride (83 mg, 0.47 mmol), as a near white solid (145 mg, 62%).

TLC $R_f$ 0.21 (10% MeOH—CH$_2$Cl$_2$)

INTERMEDIATE 56
(RS)-N-[2-[(1,1-Dimethylethyl)mercapto]-5-(2-pyrazinylcarbonyl) aminopentanoyl]-L-leucyl-L-phenylalanine N-methyl amide From intermediate 45 (200 mg, 0.42 mmol) and pyrazinoyl chloride (85 mg, 0.47 mmol), as a near white solid (145 mg, 62%).

TLC $R_f$ 0.18 (10% MeOH—CH$_2$Cl$_2$)

INTERMEDIATE 57
(RS)-N-[2-[(2-Nitrophenylsulphanyl)mercapto]-5-(acetyl) amino pentanoyl]-L-leucyl-L-phenylalanine N-methyl amide 2-Nitrosulphenyl chloride (3.26 g, 6.26 mmol) was added to a stirred solution of intermediate 46 (1.23 g, 6.49 mmol) in glacial acetic acid (75 ml) and the mixture stirred at RT overnight. The solvent was removed in vacuo and the residue purified by flash column chromatography (eluting with 5% methanol in dichloromethane) to provide the title compound (3.74 g, 97%) as a yellow solid.

TLC $R_f$ 0.34 (10% MeOH—CH$_2$Cl$_2$)

Similarly prepared were:

INTERMEDIATE 58
(RS)-N-[2-[(2-Nitrophenylsulphanyl)mercapto]-5-(benzoylamino)pentanoyl]-L-leucyl-L-phenylalanine N-methyl amide From intermediate 47 (1.08 g, 5.67 mmol), as a yellow solid (3.43 g, 99%).

TLC $R_f$ 0.54 (10% MeOH—CH$_2$Cl$_2$)

INTERMEDIATE 59
(RS)-N-[2-[(2-Nitrophenylsulphanyl)mercapto]-5-succinimido pentanoyl]-L-leucyl-L-phenylalanine N-methyl amide From intermediate 48 (618 g, 1.1 mmol), as a yellow solid (665 mg, 92%).

TLC $R_f$ 0.25 (10% MeOH—CH$_2$Cl$_2$)

INTERMEDIATE 60
(RS)-N-[2-[(2-Nitrophenylsulphanyl)mercapto]-5-(methanesulphonyl)aminopentanoyl]-L-leucyl-L-phenylalanine N-methyl amide From intermediate 49 (1.78 g, 3.27 mmol), as a yellow solid (1.84 g, 88%).

TLC $R_f$ 0.32 (10% MeOH—CH$_2$Cl$_2$)

INTERMEDIATE 61
(RS)-N-[2-[(2-Nitrophenylsulphanyl)mercapto]-5-(benzenesulphonyl)aminopentanoyl]-L-leucyl-L-phenylalanine N-methyl amide From intermediate 50 (2.25 g, 3.71 mmol), as a yellow solid (1.6 g, 68%).

TLC $R_f$ 0.37 (10% MeOH—CH$_2$Cl$_2$)

INTERMEDIATE 62
(RS)-N-[2-[(2-Nitrophenylsulphanyl)mercapto]-5-(methoxycarbonyl)aminopentanoyl]-L-leucyl-L-phenylalanine N-methyl amide From intermediate 51 (196 mg, 0.31 mmol), as a yellow solid (86 mg, 38%).

TLC $R_f$ 0.25 (10% MeOH—CH$_2$Cl$_2$)

INTERMEDIATE 63
(RS)-N-[2-[(2-Nitrophenylsulphanyl)mercapto]-5-(benzyloxycarbonyl)aminopentanoyl]-L-leucyl-L-phenylalanine N-methyl amide From intermediate 52 (229 mg, 0.32 mmol), as a yellow solid (155 mg, 60%).

TLC $R_f$ 0.37 (10% MeOH—CH$_2$Cl$_2$)

INTERMEDIATE 64
(RS)-N-[2-[(2-Nitrophenylsulphanyl)mercapto]-5-4-pyridylcarbonyl)aminopentanoyl]-L-leucyl-L-phenylalanine N-methyl amide From intermediate 53 (1.92 g, 3.29 mmol), as a yellow solid (1.66 g, 74%).

TLC $R_f$ 0.29 (10% MeOH—CH$_2$Cl$_2$)

INTERMEDIATE 65
(RS)-N-[2-[(2-Nitrophenylsulphanyl)mercapto]-5(3-pyridylcarbonyl)aminopentanoyl]-L-leucyl-L-phenylalanine N-methyl amide From intermediate 54 (190 mg, 0.33 mmol), as a yellow solid (85 mg, 38%).

TLC $R_f$ 0.24 (10% MeOH—$CH_2Cl_2$)

INTERMEDIATE 66
(RS)-N-[2-[(2-Nitrophenylsulphanyl)mercapto]-5-(2-pyridylcarbonyl)aminopentanoyl]-L-leucyl-L-phenylalanine N-methyl amide From intermediate 55 (210 mg, 0.36 mmol), as a yellow solid (120 mg, 54%).

TLC $R_f$ 0.21 (10% MeOH—$CH_2Cl_2$)

INTERMEDIATE 67
(RS)-N-[2-[(2-Nitrophenylsulphanyl)mercapto]-5-(2-pyrazinylcarbonyl)aminopentanoyl]-L-leucyl-L-phenylalanine N-methyl amide From intermediate 56 (300 mg, 0.51 mmol), as a yellow solid (110 mg, 42%).

TLC $R_f$ 0.18 (10% MeOH—$CH_2Cl_2$)

INTERMEDIATE 68
(RS)-N-[2-[(2-Nitrophenylsulphanyl)mercapto]-5-aminopentanoyl]-L-leucyl-L-phenylalanine N-methyl amide TLC $R_f$ 0.16 (10% MeOH—$CH_2Cl_2$)

INTERMEDIATE 69
(R)-N-(Phenylmethoxy)carbonyl-(S-methyl)-L-cysteine

Benzyl chloroformate (11.1 ml, 65 mmol) was added dropwise to a stirred solution of (S-methyl)-L-cysteine (10 g, 75 mmol) in 2M aqueous sodium hydroxide (50 ml) and the mixture stirred at RT for 4 h. The mixture was then basified to pH14 with further 2M sodium hydroxide and the solution washed with ethyl acetate (4×50 ml). The aqueous phase was acidified to pH3 with concentrated hydrochloric acid and then extracted with ethyl acetate (4×70 ml). The combined extracts were washed with brine, dried ($MgSO_4$) and evaporated in vacuo to provide the product as a pale yellow oil (16.8 g, 84%)

TLC $R_f$ 0.21 (10% MeOH—$CHCl_3$)

INTERMEDIATE 70
(R)-N-(1,1-Dimethylethoxy)carbonyl-(S-methyl)cysteine

Di-tert-butyldicarbonate (8.88 g, 40.7 mmol) was added to a stirred solution of S-methyl-L-cysteine methyl-L-cysteine (5 g, 37 mmol) and sodium bicarbonate (7.8 g, 92.5 mmol) in a mixture if water (150 ml) and dioxane (100 ml) at 0° C. The mixture was allowed to warm to RT and stirred overnight, then diluted with water (100 ml), acidified to pH 3 using 1N hydrochloric acid then extracted with ethyl acetate (3×100 ml). The combined extracts were washed with brine, dried ($MgSO_4$) and evaporated in vacuo to provide the title compound as a colourless oil (6.64 g, 76%)

TLC $R_f$ 0.55 (MeOH—$H_2O$)

Similarly prepared was:

INTERMEDIATE 71
(S)-N-(1,1-Dimethylethoxy)carbonyl-propylglycine

From (S)-norvaline (5 g, 42.7 mmol), as a colourless oil (6.3 g, 68%).

TLC $R_f$ 0.50 (MeOH—$H_2O$)

INTERMEDIATE 72
(S)-N-(1,1-Dimethylethoxy)carbonyl-(O-methyl)serine

Sodium hydride (60% dispersion, 4.3 g, 0.107 mol) was added portionwise at 0° C. to a stirred solution of (S)-N-(1,1-dimethylethoxy)carbonylserine (10 g, 48.7 mmol) in anhydrous DMF (250 ml). A solution of iodomethane (6.1 ml, 0.1 mol) in anhydrous DMF (10 ml) was then added dropwise. The mixture was allowed to warm to RT and stirred overnight, then diluted with 1N hydrochloric acid to pH3 and the solution concentrated in vacuo to ca. 100 ml. The mixture was diluted with water (200 ml) and extracted with ethyl acetate (3×100 ml). The combined extracts were washed with brine (100 ml), dried ($MgSO_4$) and evaporated in vacuo to provide the title compound as a yellow oil (7.48 g, 70%)

TLC $R_f$ 0.39 (10% MeOH—$CH_2Cl_2$)

INTERMEDIATE 73
(RS)-N-Benzoyl-[b-(4-pyridyl)]alanine methyl ester a) 2-(4-Pyridyl)-1-(N-benzoyl)aminoethylene-1-carboxylic acid hydrochloride 4-pyridylcarboxaldehyde (85 g, 0.79 mol) was added to a stirred ice cold suspension of sodium acetate (16 g, 0.195 mol) and hippuric acid (150 g, 0.84 mol) in acetic anhydride (360 ml, 3.8 mol) an exothermic reaction ensued and the internal temperature reached 30–40° C. The mixture was cooled to RT then poured into water (1500 ml). The resulting solid was removed by filtration washed with water (2×500 ml) to provide the intermediate azlactone (74 g, 37%) as a brown solid The azlactone (70 g, 0.28 mol) was dissolved in conc. hydrochloric acid (210 ml) resulting in the rapid formation of a precipitate which was removed by filtration, washed with acetone (2×500 ml) and dried in vacuo to provide the product (71 g, 78 %) as a pale green solid.

b) (RS)-N-Benzoyl-[b-(4-pyridyl)]alanine hydrochloride

The olefin hydrochloride (70 g, 0.23 mol) was hydrogenated at RT and atmospheric pressure over 5% palladium on carbon (7 g) in water (700 ml) overnight. The catalyst was removed by filtration through celite and the solvent concentrated to a volume of ca. 100 ml. Acetone (1000 ml) was added and the resulting precipitate removed by filtration and dried in vacuo to provide the product (53 g, 75%) as an off-white solid.

c) (RS)-N-Benzoyl-[b-(4-pyridyl)]alanine methyl ester

Thionyl chloride (15 ml, 0.21 mol) was added to an ice cold solution of the acid (53 g, 0.17 mol) in methanol (200 ml). The mixture was allowed to warm to RT over 30 min before the solvent was removed in vacuo providing an off-white semi-solid. The residue was suspended in 8% sodium bicarbonate (500 ml) and the product extracted into ethyl acetate (4×400 ml). The combined organic extracts were then washed with brine (1000 ml), dried ($MgSO_4$) and evaporated in vacuo providing the title compound (46 g, 94%) as an off-white solid.

$C_{16}H_{16}N_2O_3$[284.3]; [MH$^+$ 285]

Similarly prepared were:

INTERMEDIATE 74
(RS)-N-Benzoyl-[b-(3-pyridyl)]alanine methyl ester

In three steps from pyridine-3-carboxaldehyde as a white solid.

$C_{16}H_{16}N_2O_3$[284.3]; [MH$^+$ 285]

INTERMEDIATE 75
(RS)-N-Benzoyl-2-methoxyalanine methyl ester

In three steps from 2-methoxybenzaldehyde as a white solid $C_{17}H_{19}N_2O_4$[301.3]; [MH$^+$302]

INTERMEDIATE 76
(S)-N-(1,1-Dimethylethoxy)carbonyl-[b-(4-pyridyl)]alanine

Intermediate 73 (27 g, 0.104 mol) was dissolved in hot acetone (50 ml) and the solution added to 0.03M potassium dihydrogen phosphate (500 ml) at pH7.2.

Alcalase (1 ml) was then added to the vigorously stirred solution and the pH maintained at 7.2 by the addition of 1M sodium hydroxide (ca. 20 ml) over 30 min. Undissolved ester was filtered off and the filtrate washed with ethyl acetate (4×250 ml). The solvent was then evaporated in vacuo, the residue dissolved in 6N hydrochloric acid (100 ml) then heated under reflux for 5 h. After cooling to RT the precipitated benzoic acid was removed by filtration and the filtrate washed with ethyl acetate (2×100 ml). The aqueous portion was then evaporated in vacuo to provide the optically pure amino-acid as its dihydrochloride salt (9.48 g, 81%).

The dihydrochloride salt was dissolved in water (150 ml) and treated with Amberlite IRA-67 ion exchange resin to pH 8. The resin was removed by filtration through celite and the solution evaporated in vacuo to provide the free amino-acid as a white solid (6.7 g, 100%).

Di-tert-butyldicarbonate (13 g, 60 mmol) was added to a stirred suspension of the amino-acid in a mixture of tert-butanol (100 ml) and water (50 ml) while the pH was maintained at 8.5 by the addition of 1M sodium hydroxide (55 ml) over 40 min. Water (50 ml) was added, the mixture washed with heptane (2×100 ml) then acidified to pH 3.5 by the addition of solid potassium hydrogen sulphate. The mixture was then evaporated to dryness and the residue triturated with methanol (3×150 ml) to extract the product. Evaporation of the solvent in vacuo provided the title compound as a white solid which was recrystallised from aqueous ethanol to optical purity (3.27 g, 61%).

$[a]_D$+24.3° (c=1, Trifluoroacetic acid)

Similarly prepared were:

INTERMEDIATE 77

(S)-(1,1-Dimethylethoxy)carbonyl-[b-(3-pyridyl)]alanine

From intermediate 74 as a white solid $[a]_D$+16.1° (c=1, Trifluoroacetic acid)

INTERMEDIATE 78

(S)-(1,1-Dimethylethoxy)carbonyl-2-methoxyphenylalanine

From intermediate 75 as a white solid (11.1 g, 97%)

$[a]_D$−15.2° (c=1, MeOH)

INTERMEDIATE 79

(RS)-N-Acetyl-[b-(2-pyridyl)]alanine

A solution of sodium methoxide (65.8 g, 1.22 mol) in methanol (300 ml) was treated portionwise with diethylacetamidomalonate (132.3 g, 0.61 mol) maintaining a temperature of ca. 45° C. The mixture was then heated under reflux for 15 min. The mixture was cooled to 50° C. then treated slowly with a suspension of 2-chloromethylpyridine hydrochloride (100 g, 0.61 mol), the pink suspension was then heated under reflux for a further 6 h. Water (500 ml) was added followed by 10M sodium hydroxide (122 ml, 1.22 mol) and the pH was maintained at ca. 11 while heating the mixture at 70° C. overnight. The mixture was cooled to RT and the methanol removed in vacuo. The aqueous residue was washed with ethyl acetate (2×500 ml), then acidified to pH 5 and further washed with ethyl acetate (2×500 ml), before evaporating in vacuo to provide a semi-solid. The residue was triturated with hot ethanol (500 ml) and the sodium chloride removed by filtration. The filtrate was then evaporated in vacuo and the residue crystallised from methanol-ethyl acetate to provide the title compound (70 g, 66%) as a yellow solid.

TLC $R_f$ 0.5 [n-BuOH-AcOH-pyridine-$H_2O$ (15-3-10-12)]

Similarly prepared were:

INTERMEDIATE 80

(RS)-N-Acetyl-[b-(4-thiazolyl)]alanine

From 4-(chloromethyl)thiazole, as a white foam (6.7 g, 73%).

TLC Rf 0.37 (1% AcOH-20% Hexane-EtOAc)

INTERMEDIATE 81

(S)-(1,1-Dimethylethoxy)carbonyl-[b-(2-pyridyl)]alanine

A suspension of intermediate 79 (65 g, 0.31 mol) in aqueous potassium dihydrogen orthophosphate (10 mM, 650 ml) was warmed to 40° C. and the resulting mixture (pH 4) basified to pH 8 with 10M sodium hydroxide (10 ml) forming a solution. Acylase 30,000 (1.3 g) was added and the mixture incubated at 40° C. overnight. The resulting suspension was cooled to RT, the solid removed by filtration, then the filtrate acidified to pH 1 with 2N hydrochloric acid and washed with ethyl acetate (2×300 ml). The aqueous portion was evaporated in vacuo to provide a semi-solid which was triturated with hot methanol (300 ml) and the solid removed by filtration. To the cooled solution was then added 5M sodium hydroxide to pH 10, followed by di-tert-butyldicarbonate (28.6 g, 0.131 mol), the mixture was maintained at pH 10 by the addition of 5M sodium hydroxide (44 ml) over a period of 6 h. The methanol was then removed in vacuo, the aqueous residue washed with ether (2×500 ml) then acidified to pH 3 with 1M potassium hydrogen sulphate. The mixture was extracted with ethyl acetate (4×500 ml), the combined extracts washed with brine (500 ml), dried ($MgSO_4$) and evaporated in vacuo to provide the crude product which was crystallised from ethyl acetate as a white solid (11.6 g, 23%).

$[a]_D$−16.0° (c=1, MeOH)

Similarly prepared were:

INTERMEDIATE 82

(S)-N-(1,1-Dimethylethoxy)carbonyl-[b-(4-thiazolyl)]alanine

From intermediate 80, as a white solid (11 g, 94%)

HPLC (Chirex (D)-penicillamine; 2 mM $CuSO_4$; 0.7 ml/min; RT=3.25 min; 99% ee.

INTERMEDIATE 83

(S)-N-(1,1-Dimethylethoxy)carbonyl-[b-(2-pyridyl)]alanine N-methyl amide

DCC (4.07 g, 19.7 mmol) was added to an ice cooled solution of intermediate 81 (5.0 g, 18.8 mmol) and N-hydroxysuccinimide (2.27 g, 19.7 mmol) in dry tetrahydrofuran (200 ml). After stirring at RT for 3 h the mixture was treated with 40% w/v aqueous methylamine (6.8 ml, 79 mmol) and stirred for a further 2 h. The precipitated solid was removed by filtration, the filtrate evaporated in vacuo and the residue dissolved in dichloromethane (100 ml). The solution was washed sequentially with water (2×100 ml), 8% sodium bicarbonate (2×100 ml) and brine (100 ml), dried ($MgSO_4$) and evaporated in vacuo to provide the crude product.

Purification by column chromatography eluting with 2–5% methanol/dichloromethane provided the title compound (2.7 g, 51%) as a red foam.

TLC $R_f$ 0.38 (3% MeOH—$CH_2Cl_2$)

Similarly prepared were:

INTERMEDIATE 84

(S)-N-(1,1-Dimethylethoxy)carbonyl-L-[b-(4-thiazolyl(] alanine N-methyl amide

From intermediate 82, as a white solid (3.0 g, 64%).

TLC $R_f$ 0.46 (5% MeOH—$CH_2Cl_2$)

INTERMEDIATE 85
(R)-N-(1,1-Dimethylethoxy)carbonylpenicillamine N-methyl amide A solution of (R)-N-(1,1-dimethylethoxy)carbonylpenicillamine (14 g, 56.1 mmol), N-hydroxybenzotriazole (7.6 g, 56.1 mmol), methylamine hydrochloride (18.9 g, 280 mmol), N-methylmorpholine (34 ml, 308 mmol, 4-dimethylaminopyridine (685 mg, 5.6 mmol) and EDC (11.8 g, 62 mmol) in anhydrous dimethylformamide (300 ml) was stirred at RT overnight. The mixture was poured into 10% w/v citric acid (750 ml) and extracted with ether (3×500 ml). The combined extracts were then washed with 8% sodium bicarbonate (2×500 ml) and brine (500 ml), dried ($MgSO_4$) and evaporated in vacuo to provide the title compound (12.3 g, 83%)

TLC $R_f$ 0.47 (50% hexane-EtOAc)

Similarly prepared was:

INTERMEDIATE 86
(1,1-Dimethylethoxy)carbonyl-5-methyl-L-glutamic acid N-methyl amide From (1,1-dimethylethoxy)carbonyl-5-methyl-L-glutamic acid, as a white solid (5.4 g, 94%).

TLC $R_f$ 0.21 (2% MeOH—$CH_2Cl_2$)

INTERMEDIATE 87
(S)-$N_d$-(1,1-Dimethylethoxy)carbonyl-$N_a$-(benzyloxy)carbonylornithine N-methyl amide From (S)-$N_d$-(1,1-dimethylethoxy)carbonyl-$N_a$-(benzyloxy)carbonylornithine (11.5 g, 31.4 mmol), as a white solid (11.0 g, 94%).

TLC $R_f$ 0.65 (3% MeOH—$CH_2Cl_2$)

INTERMEDIATE 88
(S)-N-(1,1-Dimethylethoxy)carbonyl-2-methoxyphenylalanine N-methyl amide From intermediate 78 (500 mg, 1.69 mmol), as a white solid (380 mg, 73%).

TLC $R_f$ 0.55 (5% MeOH—$CH_2Cl_2$)

INTERMEDIATE 89
(S)-N-(1,1-Dimethylethoxy)carbonyl-b-(3-pyridyl)alanine N-methyl amide From intermediate 77 (2.0 g, 7.5 mmol), as a white solid (1.0 g, 48%).

TLC $R_f$ 0.42 (5% MeOH—$CH_2Cl_2$)

INTERMEDIATE 90
(S)-N-(1,1-Dimethylethoxy)carbonyl-b-(4-pyridyl)alanine N-methyl amide From intermediate 76 (2.0 g, 7.5 mmol), as a white solid (1.7 g, 81%).

TLC $R_f$ 0.38 (5% MeOH—$CH_2Cl_2$)

INTERMEDIATE 91
(R)-N-(1,1-Dimethylethoxy)carbonyl-(S-methyl)penicillamine N-methyl amide A solution of iodomethane (0.59 ml, 9.55 mmol) in methanol (5 ml) was added dropwise at 0° C. to a stirred solution of intermediate 85 (500 mg, 1.51 mmol) in a mixture of 2M sodium hydroxide (5 ml) and methanol (15 ml). The mixture was stirred at RT overnight, then the methanol removed in vacuo, the residue diluted with water (50 ml) and extracted with ether (3×50 ml). The combined extracts were washed with brine, dried ($MgSO_4$) and evaporated in vacuo to provide the title compound as a colourless oil (540 mg, 99%).

TLC $R_f$ 0.47 (50% hexane-EtOAc)

INTERMEDIATE 92
(R)-N-(1,1-Dimethylethoxy)carbonyl-2,2-dimethyl-2-methane sulphonylalanine N-methyl amide A suspension of Oxone (1.02 g, 1.66 mmol) in water (5 ml) was added to a stirred solution of intermediate 91 (153 mg, 0.55 mmol) in methanol (5 ml) at 0° C., the mixture was allowed to warm to RT and stirred for 4 h. The mixture was diluted with water (50 ml) and extracted with ethyl acetate (3×50 ml). The combined extracts were washed with brine (50 ml), dried ($MgSO_4$) and evaporated in vacuo to provide the title compound as a colourless oil (101 mg, 59%).

TLC $R_f$ 0.35 (50% hexane-EtOAc)

INTERMEDIATE 93
(R)-N-(1,1-Dimethylethoxy)carbonyl-2,2-dimethyl-2-methane sulphinylalanine N-methyl amide A solution of 3-chloroperbenzoic acid (670 mg, 2.89 mmol) in dichloromethane (25 ml) was added to a stirred solution of intermediate 91 (800 mg, 2.89 mmol) in dichloromethane (25 ml) at 0° C., the mixture was allowed to warm to RT and stirred overnight. The mixture was washed sequentially with 10% w/v sodium sulphite (2×50 ml), 8% sodium bicarbonate (2×50 ml) and brine (50 ml), dried ($MgSO_4$) and evaporated in vacuo to provide the crude product as a colourless oil. Purification by flash column chromatography (eluting with 10% methanol-dichloromethane) provided the title compound as a colourless oil (470 mg, 55%).

TLC $R_f$ 0.05 (50% hexane-EtOAc)

INTERMEDIATE 94
(R)-N-2,2-Dimethyl-2-methanesulphinylalanine N-methyl amide hydrochloride A solution of intermediate 93 (470 mg, 1.61 mmol) in a mixture of dioxane (25 ml) and 2M hydrochloric acid (25 ml) was stirred at RT overnight. The solvent was evaporated to dryness in vacuo and freeze dried overnight to provide the title compound (370 mg, 100%) as a colourless gum.

TLC $R_f$ 0.06 (1% $NEt_3$-10% MeOH—$CH_2Cl_2$)

Similarly prepared were:

INTERMEDIATE 95
(R)-N-2,2-Dimethyl-2-methanesulphonylalanine N-methyl amide hydrochloride From intermediate 92 (300 mg, 0.97 mmol), as a colourless foam (210 mg, 100%).

TLC $R_f$ 0.10 (1% $NEt_3$-10% MeOH—$CH_2Cl_2$)

INTERMEDIATE 96
(R)-Penicillamine N-methyl amide hydrochloride

From intermediate 85 (300 mg, 1.14 mmol), as a colourless foam (230 mg, 100%).

TLC $R_f$ 0.13 (1% $NEt_3$-10% MeOH—$CH_2Cl_2$)

INTERMEDIATE 97
(S)-b-(3-Pyridyl)alanine N-methyl amide dihydrochloride

From intermediate 89 (1.2 g, 4.29 mmol), as a white solid (1.1 g, 100%).

TLC $R_f$ 0.05 (1% $NEt_3$-10% MeOH—$CH_2Cl_2$)

INTERMEDIATE 98
(S)-b-(4-Pyridyl)alanine N-methyl amide dihydrochloride

From intermediate 90 (1.6 g, 5.73 mmol), as a white solid (1.45 g, 100%).

TLC $R_f$ 0.08 (1% $NEt_3$-10% MeOH—$CH_2Cl_2$)

INTERMEDIATE 99
(S)-b-(2-Pyridyl)alanine N-methyl amide dihydrochloride

From intermediate 83 (1.4 g, 5.01 mmol), as a white solid (1.27 g, 100%).

TLC $R_f$ 0.13 (1% $NEt_3$-10% MeOH—$CH_2Cl_2$)

INTERMEDIATE 100
(S)-b-(4-Thiazolyl)alanine N-methyl amide hydrochloride

From intermediate 84 (1.0 g, 3.5 mmol), as a white solid (730 mg, 94%).

TLC $R_f$ 0.21 (1% NEt$_3$-10% MeOH—CH$_2$Cl$_2$)

INTERMEDIATE 101
(R)-(S-Methyl)penicillamine N-methyl amide trifluoroacetate A solution of intermediate 91 (200 mg, 0.72 mmol) in dichloromethane (4 ml) containing trifluoroacetic acid (2 ml) was stirred at RT overnight. The solvent was removed in vacuo and any excess trifluoroacetic acid removed by azeotropic distillation with heptane (3×20 ml) to provide the title compound (196 mg, 94%) as a colourless foam.

TLC $R_f$ 0.32 (1% NEt$_3$-10% MeOH—CH$_2$Cl$_2$)

Similarly prepared were:

INTERMEDIATE 102
(S)-2-(Methoxyphenyl)alanine N-methyl amide trifluoroacetate From intermediate 88 (200 mg, 0.65 mmol), as a pale yellow foam (209 mg, 100%).

TLC $R_f$ 0.25 (1% NEt$_3$-10% MeOH—CH$_2$Cl$_2$)

INTERMEDIATE 103
(S)-5-(Methyl-glutamic acid N-methyl amide trifluoroacetate From intermediate 86 (707 mg, 2.58 mmol), as a white solid (728 mg, 98%).

TLC $R_f$ 0.37 (1% NEt$_3$-10% MeOH—CH$_2$Cl$_2$)

INTERMEDIATE 104
(S)-N$_d$-(1,1-Dimethylethoxy)carbonylornithine N-methyl amide Intermediate 87 (11 g, 29 mmol) was hydrogenated at RT and atmospheric pressure over 10% palladium on carbon (1 g) in ethanol overnight. The catalyst was removed by filtration through hyflo and the filtrate evaporated in vacuo to provide the title compound (2.6 g, 36%) as a colourless oil.

TLC $R_f$ 0.37 (5% MeOH—CH$_2$Cl$_2$)

INTERMEDIATE 105
N-(Phenylmethoxy)carbonyl-(S-methyl-L-cysteinyl-L-phenylalanine N-methyl amide EDC (10.5 g, 55 mmol) was added to a stirred solution of L-phenylalanine N-methyl amide (8.9 g, 50 mmol), intermediate 69 (13.8 g, 50 mmol) and N-hydroxybenzotriazole (8.1 g, 60 mmol) in dry tetrahydrofuran (100 ml). The mixture was stirred at RT overnight. The mixture was treated with 1M hydrochloric acid (300 ml) then extracted with ethyl acetate (4×200 ml). The combined organic extracts were washed with 8% sodium bicarbonate (2×200 ml), water (200 ml) and brine (200 ml), dried (MgSO$_4$) and evaporating in vacuo to provide the product as a white solid (16.5 g, 75%)

TLC $R_f$ 0.47 (10% MeOH—CHCl$_3$)

INTERMEDIATE 106
N-(1,1-Dimethylethoxy)carbonyl-(S)-propylglycinyl-L-phenylalanine N-methyl amide From intermediate 71 (5 g, 23 mmol) and L-phenylalanine N-methyl amide (4.1 g, 23 mmol), as a white solid (7.72 mg, 89%).

TLC $R_f$ 0.48 (10% MeOH—CH$_2$Cl$_2$)

INTERMEDIATE 107
N-(1,1-Dimethylethoxy)carbonyl-L-leucyl-L-tert-leucine N-methyl amide From N-(1,1dimethylethoxy)carbonyl-L-leucine (13.07 g, 56 mmol) and L-tert-leucine N-methyl amide (8.11 g, 56 mmol), as a white solid (15.77 g, 79%).

TLC $R_f$ 0.25 (5% MeOH—CH$_2$Cl$_2$)

INTERMEDIATE 108
N-(1,1-Dimethylethoxy)carbonyl-(S)-(S-methyl)cysteinyl-L-tert-leucine N-methyl amide From intermediate 70 (6.64 g, 28 mmol) and L-tert-leucine N-methyl amide (4.07 g, 28 mmol), as a white solid (4.26 g, 42%).

TLC $R_f$ 0.45 (10% MeOH—CH$_2$Cl$_2$)

INTERMEDIATE 109
N-(1,1-Dimethylethoxy)carbonyl-(S)-(O-methyl)serinyl-L-tert-leucine N-methyl amide From intermediate 72 (7.48 g, 34 mmol) and L-tert-leucine N-methyl amide (4.92 g, 34 mmol), as a white solid (4.26 g, 42%).

TLC $R_f$ 0.40 (10% MeOH—CH$_2$Cl$_2$)

INTERMEDIATE 110
N-(Phenylmethoxy)carbonyl-L-valinyl-N$_d$-(1,1-dimethylethoxy) carbonyl-L-ornithine N-methyl amide From intermediate 104 (2.6 g, 10.6 mmol) and N-(Phenylmethoxy)carbonyl-L-valine (2.82 g, 11.2 mmol), as a white solid (3.0 g, 61%).

TLC $R_f$ 0.32 (5% MeOH—CH$_2$Cl$_2$)

INTERMEDIATE 111
(S-Methyl)-L-cysteinyl-L-phenylalanine N-methyl amide

A solution of intermediate 105 (2.0 g, 4.65 mmol) in dichloromethane (10 ml) was treated with 25% hydrobromic acid in acetic acid (18.6 ml) and the mixture stirred at RT for 1 h. Water (10 ml) was added and the mixture washed with dichloromethane (3×15 ml). The aqueous phase was then basified to pH14 with 5M sodium hydroxide then extracted with dichloromethane (4×30 ml). The combined organic extracts were then washed with brine (30 ml), dried (MgSO$_4$) and evaporated in vacuo to provide the product as a white solid (1.22 mg, 88%).

TLC $R_f$ 0.31 (10% MeOH—CHCl$_3$)

INTERMEDIATE 112
L-Valinyl-N$_d$-(1,1-dimethylethoxy)carbonyl-L-ornithine N-methylamide Intermediate 110 (3.0 g, 6.5 mmol) was hydrogenated at RT and atmospheric pressure over 10% palladium on carbon (300 mg) in ethanol (100 ml) overnight. The catalyst was removed by filtration through hyflo and the filtrate evaporated in vacuo to provide the title compound (2.2 g, 99%) as a white solid.

TLC $R_f$ 0.26 (10% MeOH—CH$_2$Cl$_2$)

INTERMEDIATE 113
(S)-Propylglycinyl-L-phenylalanine N-methyl amide

A solution of intermediate 106 (5.36 g, 14.2 mmol) in a mixture of dioxane (250 ml) and 2M hydrochloric acid (250 ml) was stirred at RT overnight. The solvent was evaporated to dryness in vacuo to provide a white solid. The residue was dissolved in water (200 ml) washed with dichloromethane (3×100 ml) then basified to pH 10 with 2M sodium hydroxide and extracted with dichloromethane (4×100 ml). The combined extracts were washed with brine (100 ml), dried (MgSO$_4$) and evaporated in vacuo to provide the title compound as a white solid (1.45 g, 37 %).

TLC $R_f$ 0.29 (10% MeOH—CH$_2$Cl$_2$)

Similarly prepared were:

INTERMEDIATE 114
(S)-(S-Methyl)cysteinyl-L-tert-leucine N-methyl amide
From intermediate 108, as a white solid (3.5 g, 97%).
TLC R$_f$ 0.45 (10% MeOH—CH$_2$Cl$_2$)

INTERMEDIATE 115
(S)-(O-Methyl)serinyl-L-tert-leucine N-methyl amide
From intermediate 109, as a white solid (2.7 g, 98%).
TLC R$_f$ 0.40 (10% MeOH—CH$_2$Cl$_2$)

INTERMEDIATE 116
L-Leucyl-L-tert-leucine N-methyl amide
From intermediate 107, as a white solid (11.2 g, 99%).
TLC R$_f$ 0.57 (10% MeOH—CH$_2$Cl$_2$)

INTERMEDIATE 117
(R)-2-Bromo-5-phthalimidopentanoic acid

A solution of D-ornithine hydrochloride (35 g, 0.208 mol) in water (350 ml) was treated with copper (II) sulphate (16.6 g, 0.104 mol). 5M Potassium hydroxide (ca. 40 ml) was added to pH 3 then N-carboethoxyphthalimide (45.5 g, 0.208 mol) was added and the pH maintained at 9–10 by the addition of 5M potassium hydroxide (ca. 55 ml). After 2 h, 48% hydrobromic acid was added to pH 0.4 (ca. 77 ml) and any resulting precipitate removed by filtration. The filtrate was cooled to <5° C., then treated with further hydrobromic acid (152 ml) and potassium bromide (59 g, 0.5 mol). The mixture was then treated dropwise over 45 min with a solution of sodium nitrite (28.6 g, 0.41 mol) in water (275 ml) whilst maintaining a temperature of <5° C. The mixture was then stirred at <5° C. overnight. The resulting precipitate was then removed by filtration, dissolved in ethyl acetate (400 ml) and the solution washed with water (2×200 ml) and brine (200 ml), dried (MgSO$_4$) and evaporated in vacuo to provide the title compound (40.6 g, 47%) as a cream solid.

TLC R$_f$ 0.80 (10% MeOH—CH$_2$Cl$_2$)

Similarly prepared was:

INTERMEDIATE 118
(S)-2-Bromo-5phthalimidopentanoic acid
From L-ornithine hydrochloride (20 g, 0.118 mol), as a cream solid (22 g, 57%).
TLC R$_f$ 0.80 (10% MeOH—CH$_2$Cl$_2$)

INTERMEDIATE 119
(S)-2-Acetylmercapto-5-phthalimidopentanoic acid
Was prepared by the previously described procedure from intermediate 117 (39.9 g, 0.11 mol), as a pale orange oil (35.6 g, 99%).
TLC R$_f$ 0.24 (50% Heptane-EtOAc)

INTERMEDIATE 120
(S)-2-Acetylmercapto-5-phthalimidopentanoic acid
Was prepared by the previously described procedure from intermediate 118 (20 g, 56 mmol), as a pale orange oil (17.7 g, 99%).
TLC R$_f$ 0.24 (50% Heptane-EtOAc)

INTERMEDIATE 121
(RS)-2-(Acetylmercapto)-5-phthalimidopentanoyl-L-leucine 1,1-dimethylethyl ester EDC (3.64 g, 19 mmol) was added to a stirred mixture of L-leucine 1,1-dimethylethyl ester (3.93 g, 17.6 mmol), N-hydroxybenzotriazole (2.62 g, 19.4 mmol), triethylamine (2.51 ml, 18 mmol) and intermediate 15 (5.94 g, 18.5 mmol), triethylamine (200 ml). The mixture was stirred overnight then the solvent removed in vacuo and the residue partitioned between water (100 ml) and ethyl acetate (100 ml). The aqueous portion was then extracted with ethyl acetate (2×50 ml), the combined extracts washed with water (2×100 ml) and brine (100 ml), dried (MgSO$_4$) and evaporated in vacuo to a colourless oil.

Purification by column chromatography eluting with hexane/ethyl acetate (2:1) provided the title compound (6.6 g, 77%) as a white solid, a 1:1 mixture of diastereoisomers.

TLC R$_f$ 0.42 (EtOAc/Hexane (1:1))

INTERMEDIATE 122
(RS)-2-(Acetylmercapto)-5-phthalimidopentanoyl-L-leucine

Trifluoroacetic acid (9.0 ml, 115 mmol) was added to a stirred solution of intermediate 121 (3.0 g, 6.1 mmol) in dry dichloromethane (40 ml) and the mixture stirred at RT overnight. The mixture was concentrated in vacuo and the excess trifluoroacetic acid removed by azeotroping with heptane to provide the title compound (2.48 g, 94%) as a colourless foam, a 1:1 mixture of diastereoisomers.

TLC R$_f$ 0.42 (EtOAc/Hexane (3:2))

INTERMEDIATE 123
(RS)-2-Acetylmercapto)-4-succinimidobutanoic acid
Was prepared by the procedure previously described for intermediate 36
TLC R$_f$ 0.38 (HOAc/EtOAc/Hexane (0.1:1:1))

INTERMEDIATE 124
(S-Methyl)-L-cysteinyl-L-tryptophan N-methyl amide
Was prepared by the procedure previously described for intermediate 111
TLC R$_f$ 0.45 (EtOAc/Hexane (1:1))

INTERMEDIATE 125
(RS)-2-[(1,1-Dimethylethyl)mercapto]-3-phthalimidopropananoic acid
Was prepared by the procedure previously described for intermediate 43.
TLC R$_f$ 0.48 (HOAc/EtOAc/Hexane (0.1:1:1))

EXAMPLE 1
(RS)-N-[2,3-Bis-acetylmercaptopropanoyl]-L-leucyl-L-phenylalanine N methyl amide EDC (198 mg) was added to a solution of intermediate 14 (209 mg), L-leucyl-L-phenylalanine N-methyl amide (274 mg), and N-hydroxybenzotriazole hydrate (153 mg) in dry THF (10 ml) at 0° C., and the mixture was stirred at that temperature until TLC analysis (5% MeOH—CH$_2$Cl$_2$) indicated a complete consumption of starting materials (72 h). The solvent was removed by evaporation and the residue was partitioned between 1N hydrochloric acid (35 ml) and ethyl acetate (50 ml). The organic layer was separated, washed with aqueous sodium bicarbonate solution (2×200 ml) and brine (2×20 ml), then dried (MgSO$_4$) and evaporated in vacuo to give the crude product. Purification by flash column chromatography (eluting with 2–5% methanol-dichloromethane) gave the title compound as a colourless solid (264 mg).

TLC R$_f$ 0.25 (2% MeOH—CH$_2$Cl$_2$)
Similarly prepared were:

EXAMPLE 2
(RS)-N-[(2,4-Bis-acetylmercapto)butanoyl]-L-leucyl-L-phenylalanine N-methyl amide
From intermediate 15 (870 mg, 3.7 mmol) and L-leucyl-L-phenylalanine N-methyl amide (1.07 g, 3.7 mmol), as a white solid (1.4 g, 74%).
C$_{24}$H$_{35}$N$_3$O$_5$S$_2$ [509.7]; [MH$^+$=510]

EXAMPLE 3
(RS)-N-[(2,5-Bis-acetylmercapto)pentanoyl]-L-leucyl-L-phenylalanine N-methyl amide From intermediate 16 (906 mg, 3.6 mmol) and L-leucyl-L-phenylalanine N-methyl amide (1.06 g, 3.6 mmol), as a white solid (1.5 g, 79%).
$C_{25}H_{37}N_3O_5S_2$ [523.7]; [MH$^+$=524]

EXAMPLE 4
(RS)-N-[(2,6-Bis-acetylmercapto)hexanoyl]-L-leucyl-L-phenylalanine N-methyl amide From intermediate 17 (895 mg, 3.4 mmol) and L-leucyl-L-phenylalanine N-methyl amide (991 mg, 3.4 mmol), as a white solid (1.4 g, 74%).
$C_{26}H_{39}N_3O_5S_2$ [537.75]; [MH$^+$=538]

EXAMPLE 5
(RS)-N-[2-Acetylmercapto-3-methoxycarbonylpropranoyl]-L-leucyl-L-phenylalanine N-methyl amide From Intermediate 4 (0.26 g, as colourless solid (0.33 g).
$C_{23}H_{33}N_3O_6S$ [479.6]; [MH$^+$=480]

EXAMPLE 6
(RS)-N-[2-Acetylmercapto-4-methoxycarbonylbutanoyl]-L-leucyl-L-phenylalanine N-methyl amide From Intermediate 5 (0.40 g, as colourless solid (0.67 g).
$C_{24}H_{35}N_3O_6S$ [493.6]; [MH$^+$=494]

EXAMPLE 7
(RS)-N-[2-Acetylmercapto-5-methoxycarbonylpentanoyl]-L-leucyl-L-phenylalanine N-methyl amide From Intermediate 6 (0.9 g, as colourless solid (1.1 g).
$C_{25}H_{37}N_3O_6S$ [507.6]; [MH$^+$=508]

EXAMPLE 8
(RS)-N-[2-Acetylmercapto-6-methoxycarbonylhexanoyl]-L-leucyl-L-phenylalanine N-methyl amide From Intermediate 7 (0.95 g, as colourless solid (1.0 g).
$C_{26}H_{39}N_3O_6S$ [521.6]; [MH$^+$=522]

EXAMPLE 9
(RS)-N-[2-Acetylmercapto-5-phthalimidopentanoyl]-L-leucyl-L-tryptophan N-methyl amide From Intermediate 36 (730 mg, and L-leucyl-L-tryptophan N-methyl amide (700 mg), as a pale yellow foam (1.0 g, 74%).
$C_{33}H_{39}N_5O_6S$ [633.7]; [MH$^+$=634]

EXAMPLE 10
(RS)-N-[2-Acetylmercapto-6-methoxycarbonylhexanoyl]-L-leucyl-L-tryptophan N-methyl amide From Intermediate 7 (375 mg, and L-leucyl-L-tryptophan N-methyl amide (500 mg), as a pale yellow foam (440 mg, 52%).
$C_{28}H_{40}N_4O_6S$ [560.7]; [MH$^+$=561]

EXAMPLE 11
(RS)-N-[2-Acetylmercapto-5-phthalimidopentanoyl]-L-valinyl-L-phenylalanine N-methyl amide From Intermediate 36 (232 mg, and L-valinyl-L-phenylalanine N-methyl amide (200 mg), as a white solid (230 mg, 55%).
$C_{30}H_{36}N_4O_6S$ [580.7]; [MH$^+$=581]

EXAMPLE 12
(RS)-N-[2-Acetylmercapto-6-methoxycarbonylhexanoyl]-L-valinyl-L-phenylalanine N-methyl amide From Intermediate 7 (179 mg, and L-valinyl-L-phenylalanine N-methyl amide (200 mg), as a white solid (200 mg, 56%).
$C_{25}H_{37}N_3O_6S$ [507.6]; [MH$^+$=508]

EXAMPLE 13
(RS)-N-[2-Acetylmercapto-2-(3-phthalimidophenyl)acetyl]-L-leucyl-L-phenylalanine N-methyl amide From Intermediate 37 (690 mg, and L-leucyl-L-phenylalanine N-methyl amide (489 mg), as a white solid (927 mg, 88%).
$C_{34}H_{36}N_4O_6S$ [628.8]; [MH$^+$=629]

EXAMPLE 14
N-[2-(Acetylmercapto)-2-[3-cis-phthalimidocyclopentyl]acetyl-L-leucyl-L-phenylalanine N-methyl amide From intermediate 38 (140 mg, 0.4 mmol) and L-leucyl-L-phenylalanine N-methyl amide (117 mg, 0.4 mmol), as a tan foam (197 mg, 79%), a 1:1:1:1 of the four expected diastereoisomers.
$C_{33}H_{40}N_4O_6S$ [620.8]; [MH$^+$=621]

EXAMPLE 15
N-[2-(acetylmercapto)-2-[3-trans-phthalimidocyclopentyl]acetyl-L-leucyl-L-phenylalanine N-methyl amide From intermediate 39 (235 mg, 0.7 mmol) and L-leucyl-L-phenylalanine N-methyl amide (197 mg, 0.7 mmol), as a brown foam (358 mg, 85%), a 1:1:1:1 of the four expected diastereoisomers.
$C_{33}H_{40}N_4O_6S$ [620.8]; [MH$^+$=621]

EXAMPLE 16
(S)-N-[2-(Acetylmercapto)-5-phthalimido]pentanoyl-$_L$-leucyl-(S)-tert-leucine N-methyl amide From intermediate 119 (13.8g, 43 mmol) and intermediate 116 (11.2g, 44 mmol), as a white solid (11.6 g, 48%).
$C_{28}H_{40}N_4O_6S$ [560.7]; [MH$^+$=561]

EXAMPLE 17
(S)-N-[2-(Acetylmercapto)-5-phthalimido]pentanoyl-$_L$-leucyl-$_L$-phenylalanine N-methyl amide From intermediate 119 (10 g, 31 mmol) and $_L$-leucyl-$_L$-phenylalanine N-methyl amide (9.0 g, 31 mmol), as a white solid (10.5 g, 57%).
$C_{31}H_{38}N_4O_6S$ [594.7]; [MH$^+$=595]

EXAMPLE 18
(R)-N-[2-(Acetylmercapto)-5-phthalimido]pentanoyl-$_L$-leucyl-$_L$-phenylalanine N-methyl amide From intermediate 120 (1.0 g, 3.1 mmol) and $_L$-leucyl-$_L$-phenylalanine N-methyl amide (900 mg, 3.1 mmol), as a white solid (885 mg, 48%).
$C_{31}H_{38}N_4O_6S$ [594.7]; [MH$^+$=595]

EXAMPLE 19
(S)-N-[2-(Acetylmercapto)-5-phthalimido]pentanoyl-$_L$-leucyl-$_L$-tryptophan N-methyl amide From intermediate 119 (411 mg, 1.28 mmol) and $_L$-leucyl-$_L$-trypotophan N-methyl amide (423 mg, 1.28 mmol), as a white solid (330 mg, 41%).
$C_{33}H_{39}N_5O_6S$ [633.7]; [MH$^+$=634]

EXAMPLE 20
(RS)-N-[2-(Acetylmercapto)-5-phthalimidopentanoyl]-(S-methyl)-L-cysteinyl-L-phenylalanine N-methyl amide From intermediate 36 (326 mg, 1 mmol) and intermediate 114 (350 mg, 1 mmol), as a white solid (380 mg, 64%).
$C_{29}H_{34}N_4O_6S_2$ [598.7]; [MH$^+$=599]

EXAMPLE 21
(RS)-N-[2-(Acetylmercapto)-5-phthalimido]pentanoyl-(S)-propylglycinyl-L-phenylalanine N-methyl amide From intermediate 113 (145 mg, 0.52 mmol) and intermediate 36 (168 mg, 0.52 mmol), as a white solid (160 mg, 53%).

$C_{30}H_{36}N_4O_6S$ [580.7]; [MH$^+$=581]

EXAMPLE 22
(RS)-N-[2-(Acetylmercapto)-5-phthalimido]pentanoyl-L-valinyl-N$_d$(1,1-dimethylethoxy)carbonyl-L-ornithine N-methyl amide From intermedaite 112 (508 mg, 1.47 mmol) and intermediate 36 (491 mg, 1.53 mmol), as a white solid (687 mg, 72%).

$C_{31}H_{45}N_5O_8S$ [647.8]; [MH$^+$=648]

EXAMPLE 23
(RS)-N-[2-(Acetylmercapto)-5-phthalimido]pentanoyl-L-valinyl-L-ornithine N-methyl amide trifluoroacetate A solution of example 22 (585 mg, 0.90 mmol) in dichloromethane (20 ml) containing trifluoroacetic acid (2 ml) was stirred at RT overnight. The solvent was removed in vacuo and any excess trifluoroacetic acid removed by azeotropic distillation with heptane (3×20 ml) to provide the title compound (596 mg, 99%) as a off white solid.

$C_{26}H_{38}N_5O_6S$ [548.7]; [MH$^+$=549]

EXAMPLE 24
(RS)-N-[2-(Acetylmercapto)-5-phthalimido]pentanoyl-L-valinyl-N$_d$-(acetyl-L-ornithine N-methyl amide Acetyl chloride (0.024 ml, 0.34 mmol) was added at 0° C. to a stirred solution of example 23 (205 mg, 0.31 mmol) and N-methylmorpholine (0.134 ml, 0.31 mmol) in anhydrous dichloromethane (20 ml). The mixture was allowed to warm to RT and stirred for 1 h before diluting with dichloromethane (20 ml) and washing sequentially and 2N hydrochloride (20 ml), 8% sodium bicarbonate (20 ml), water (20 ml) and brine (20 ml), dried (MgSO$_4$) and evaporated in vacuo to a colourless foam. Purification by flash column chromatography (eluting with 3–5% methanol-dichloromethane) provided the title compound (30 mg, 17%) as a white solid.

$C_{28}H_{41}N_5O_7S$ [590.7]; [MH$^+$=591]

EXAMPLE 25
(RS)-N-[2-(Acetylmercapto)-4-phthalimidobutanoyl]-$_L$-leucyl-$_L$-phenylalanine N-methyl amide A solution of potassium thiolacatate (98 mg) in methanol (2 ml) was added to a suspension of Intermediate 40 (0.5 g) in methanol (10 ml) and the mixture was stirred at RT for 30 min, then at reflux for 6 h. The solvent was then removed under reduced pressure and the residue was partitioned between water (50 ml) and dichloromethane (150 ml). The layers were separated and the organic layer was dried over sodium sulfate, filtered, and evaporated to give the crude product. Purification by flash column chromatography (eluting with 50% ethyl acetate-dichloromethane) gave the title compound as a colourless solid (270 mg).

TLC R$_f$ 0.30 (50% EtOAc—CH$_2$Cl$_2$)

Similarly prepared were:

EXAMPLE 26
(RS)-N-[2-(Acetylmercapto)-5-phthalimidopentanoyl]-$_L$-leucyl-$_L$-phenylalanine N-methyl amide From Intermediate 41 (0.5 g) as a near colourless solid (0.42 g).

TLC R$_f$ 0.20 (50% EtOAc—CH$_2$Cl$_2$)

EXAMPLE 27
(RS)-N-[2-(Acetylthio-6-phthalimidohexanoyl]-$_L$-leucyl-$_L$-phenylalamine N-methyl amide From Intermediate 42 (0.50 g) as a plae yellow solid (0.39 g).

TLC R$_f$ 0.31 (50% EtOAc—CH$_2$Cl$_2$)

EXAMPLE 28
(RS)-N-[2-(Acetylmercapto)-5-phthalimido]pentanoyl-$_L$-leucyl-$_L$-[β-(4-thiazolyl)]alanine N-methyl amide EDC (107 mg, 0.56 mmol) was aded to astirred solution of intermediate 122 (222 mg, 0.51 mmol), N-hydroxybenzotriazole 76 mg, 0.56 mmol), triethylamine (75 ml, 0.53 mmol) and intermediate 100 (113 mg, 0.51 mmol) in dry tetrahydrofuran (30 ml). The mixture was stirred at RT overnight then the solvent removed in vacuo and the residue partitioned between water (20 ml) and ethyl acetate (20 ml). The aqueous portion was then extracted with ethyl acetate (2×20 ml), the combined extracts washed with water (2×50 ml) and brine (50 ml), dried (MgSO$_4$) and evaporated in vacuo to a pale yellow oil.

Purification by column chromatography eluting with dichloromethane/methanol (98.2) provided the title compound (170 mg, 55%) as a white solid.

$C_{28}H_{35}N_5O_6S_2$ [601.7]; [MH$^+$=602]

Similarly prepared were:

EXAMPLE 29
(RS)-N-[2-(Acetylmercapto)-5-phthalimido]pentanoyl-$_L$-leucyl-$_L$-[β-(2-pyridyl)]alanine N-methyl amide From intermediate 122 and intermediate 99, as a white solid (277 mg, 67%).

$C_{30}H_{37}N_5O_6S$ [595.7]; [MH$^+$=596]

EXAMPLE 30
(RS)-N-[2-(Acetylmercapto)-5-phthalimido]pentanoyl-$_L$-leucyl-$_L$-[β-(3-pyridyl)]alanine N-methyl amide From intermediate 122 and intermediate 97, as a white solid (50 mg, 12%).

$C_{30}H_{37}N_5O_6S$ [595.7]; [MH$^+$=596]

EXAMPLE 31
(RS)-N-[2-(Acetylmercapto)-5-phthalimido]pentanoyl-$_L$-leucyl-$_L$-[β-(4-pyridyl)]alanine N-methyl amide From intermediate 122 and intermediate 98, as a white solid (310 mg, 77%).

$C_{30}H_{37}N_5O_6S$ [595.7]; [MH$^+$=596]

EXAMPLE 32
(RS)-N-[2-(Acetylmercapto)-5-phthalimido]pentanoyl-$_L$-leucyl-5-methyl-$_L$-glutamic acid N-methyl amide From intermediate 122 and intermediate 103, as a white solid (201 mg, 49%).

$C_{28}H_{38}N_4O_8S$ [590.3]; [MH$^+$591]

EXAMPLE 33
(RS)-N-[2-(Acetylmercapto)-5-phthalimido]pentanoyl-$_L$-leucyl-(S)-(2-methoxyphenyl)alanine N-methyl amide From intermediate 122 and intermediate 102, as a white solid (150 mg, 37%).

$C_{32}H_{40}H_4O_7S$ [624.8]; [MH$^+$=625]

EXAMPLE 34
(RS)-N-[2-(Acetylmercapto)-5-phthalimido]pentanoyl-$_L$-leucyl-(R)-penicillamine N-methyl amide From intermediate 122 and intermediate 96, as a white solid (230 mg, 35%).

$C_{27}H_{38}N_4O_6S_2$ [578.8]; [MH$^+$=579]

EXAMPLE 35
(RS)-N-[2-(Acetylmercapto)-5-phthalimido]pentanoyl-$_L$-leucyl-(R)-(S-methyl)-penicillamine N-methyl amide From intermediate 122 and intermediate 101, as a white solid (400 mg, 35%).

$C_{28}H_{40}N_4O_6S_2$ [592.8]; [MH$^+$=593]

EXAMPLE 36
(RS)-N-[2-(Acetylmercapto)-5-phthalimido]pentanoyl-$_L$-leucyl-(R)-(2,2-dimethyl-2-methanesulphonyl)alanine N-methyl amide From intermediate 122 and intermediate 95, as a white solid (380 mg, 66%).

$C_{28}H_{40}N_4O_8S_2$ [624.8]; [MH$^+$=625]

EXAMPLE 37
(RS)-N-[2-(Acetylmercapto)-5-phthalimido]pentanoyl-$_L$-leucyl-(R)-(2,2-dimethyl-2-methanesulphinyl)alanine N-methyl amide From intermediate 122 and intermediate 94, as a white solid (360 mg, 37%).

$C_{28}H_{40}N_4O_7S_2$ [608.8]; [MH$^+$=609]

EXAMPLE 38
(RS)-N-[2-(Acetylmercapto)-5-phthalimido]pentanoyl-$_L$-leucyl-(S)-tert-leucine N-methyl amide From intermediate 122 and tert-leucine N-methyl amide hydrochloride, as a white solid (120 mg, 25%).

$C_{28}H_{40}N_4O_6S$ [560.7]; [MH$^+$=561]

EXAMPLE 39
(RS)-N-[2-Mercapto-5-(acetyl)aminopentanoyl]-L-leucyl-L-phenylalanine N-methyl amide 0.4M Sodium hydroxide (0.82 ml) was added to a stirred solution of intermediate 57 (203 mg, 0.328 mmol) and 2-mercaptoethanol (0.23 ml, 3.38 mmol) in a methanol at 0° C. After 15 min acetic acid (0.5 ml) was added and the solvents evaporated in vacuo to provide a yellow oil. Ether (20 ml) was added and the resulting precipitate removed by filtration to provide the crude thiol. Purification by flash column chromatography (eluting with 5% methanol in dichloromethane) provided the title compound (86 mg, 56%) as a white solid.

$C_{23}H_{36}H_4O_4S$ [464.6]; [MH$^+$=465]

Similarly prepared were:

EXAMPLE 40
(RS)-N-[2-Mercapto-5-(benzoyl)aminopentanoyl]-L-leucyl-L-phenylalanine N-methyl amide From intermediate 58 (400 mg, 0.59 mmol), as a white solid (175 mg, 59%).

$C_{28}H_{38}N_4O_4S$ [526.7]; [MH$^+$=527]

EXAMPLE 41
(RS)-N-[2-Mercapto-5-(succinimido)pentanoyl]-L-leucyl-L-phenylalanine N-methyl amide From intermediate 59 (600 mg, 0.91 mmol), as a white solid (147 mg, 32%).

$C_{25}H_{36}N_4O_5S$ [504.7]; [MH$^+$=505]

EXAMPLE 42
(RS)-N-[2-Mercapto-5-(methanesulphonyl)aminopentanoyl]-L-leucyl-L-phenylalanine N-methyl amide From intermediate 60 (600 mg, 1.0 mmol), as a white solid (262 mg, 57%).

$C_{22}H_{36}N_4O_5S_2$ [500.7]; [MH$^+$=501]

EXAMPLE 43
(RS)-N-[2-Mercapto-5-(benzoylphonyl)aminopentanoyl]-L-leucyl-L-phenylalanine N-methyl amide From intermediate 61 (500 mg, 0.7 mmol), as a white solid (221 mg, 56%).

$C_{27}H_{36}N_4O_5S_2$ [562.8]; [MH$^+$=563]

EXAMPLE 44
(RS)-N-[2-Mercapto-5-(4-pyridylcarbonyl)aminopentanoyl]-L-leucyl-L-phenylalanine N-methyl amide From intermediate 64 (330 mg, 0.48 mmol), as a white solid (115 mg, 22%).

$C_{27}H_{37}N_5O_4S$ [527.7]; [MH$^+$=528]

EXAMPLE 45
(RS)-N-[2-Mercapto-5-(3-pyridylcarbonyl)aminopentanoyl]-L-leucyl-L-phenylalanine N-methyl amide From intermediate 65 (200 mg, 0.29 mmol), as a white solid (34 mg, 22%).

$C_{27}H_{37}N_5O_4S$ [527.7]; [MH$^+$=528]

EXAMPLE 46
(RS)-N-[2-Mercapto-5-(2-pyridylcarbonyl)aminopentanoyl]-L-leucyl-L-phenylalanine N-methyl amide From intermediate 66 (150 mg, 0.22 mmol), as a white solid (60 mg, 52%).

$C_{27}H_{37}N_5O_4S$ [527.7]; [MH$^+$=528]

EXAMPLE 47
(RS)-N-[2-Mercapto-5-(2-pyrazinylcarbonyl)aminopentanoyl]-L-leucyl-L-phenylalanine N-methyl amide From intermediate 67 (100 mg, 0.15 mmol), as a white solid (30 mg, 38%).

$C_{26}H_{36}N_6O_4S$ [528.7]; [MH$^+$=529]

EXAMPLE 48
(RS)-N-[2-Mercapto-5-phthalimido]pentanoyl]-$_L$-leucyl-$_L$-[β-(4-thiazolyl)]alanine N-methyl amide Concentrated ammonium hydroxide (0.5 ml) was added to a solution of example 28 (110 mg, 0.18 mmol) in methanol (10 ml) at 0° C. and the mixture was stirred at that temperataure for 3 h. The mixture was diluted with water (10 ml), acidified with 2N aqueous hydrochloric acid and extracted with dichloromethane (3×20 ml). The combined extracts were dried (Na$_2$SO$_4$) filtered and evaporated to give the crude product. Purification by flash column chromatography (eluting with 2% methanoldichloromethane) gave the title compound as a colourless solid (71 mg, 71%).

$C_{26}H_{33}N_5O_5S_2$ [559.7]; [MH$^+$=560]

Similarly prepared were:

EXAMPLE 49
(RS)-N-[2-Mercapto-5-phthalimido]pentanoyl-$_L$-leucyl-$_L$-[β-(2-pyridyl)]alanine N-methyl amide From example 29, as a white solid (75 mg, 80%).

$C_{28}H_{35}N_5O_5S$ [553.7]; [MH$^+$=554]

EXAMPLE 50
(RS)-N-[2-Mercapto-5-phthalimido]pentanoyl-$_L$-leucyl-5-methyl-$_L$-glutamic acid N-methyl amide From example 32, as a white solid (68 mg, 78%).

$C_{26}H_{36}N_4O_7S$ [548.6]; [MH$^+$=549]

EXAMPLE 51
(RS)-N-[2-Mercapto-5-phthalimido]pentanoyl-$_L$-leucyl-(R)-(S-methyl)-penicillamine N-methyl amide From example 35, as a white solid (160 mg, 70%).

$C_{26}H_{38}N_4O_5S_2$ [550.8]; [MH$^+$=551]

EXAMPLE 52
(S)-N-[2-Mercapto-5-phthalimido]pentanoyl-$_L$-leucyl-(S)-tert-leucine N-methyl amide
From example 16, as a white solid (8.12 g, 80%).
$C_{26}H_{38}N_4O_5S$ [518.7]; [MH$^+$=519]

EXAMPLE 53
(S)-N-[2-Mercapto-5-phthalimido]pentanoyl-$_L$-leucyl-$_L$-phenylalanine N-methyl amide
From example 17, as a white solid (2.7 g, 67%).
$C_{29}H_{36}N_4O_5S$ [552.7]; [MH$^+$=553]

EXAMPLE 54
(RS)-N-[2,3-Dimercaptopropanoyl]-$_L$-leucyl-$_L$-phenylalanine N-methyl amide
From example 1, as a colourless solid (76 mg).
$C_{19}H_{29}N_3O_3S_2$ [411.5]; [MH$^+$=412]

EXAMPLE 55
(RS)-N-[2-Mercapto-3-methoxycarbonylpropanoyl]-$_L$-leucyl-$_L$-phenylalanine N-methyl amide
From example 5 (0.16 g), as a colourless solid (0.14 g).
$C_{21}H_{31}N_3O_5S_2$ [437.5]; [MH$^+$=438]

EXAMPLE 56
(RS)-N-[2-Mercapto-4-methoxycarbontylbutanoyl]-$_L$-leucyl-$_L$-phenylalanine N-methyl amide
From example 6 (0.18 g), as a colourless solid (0.16 g).
$C_{22}H_{33}N_3O_5S$ [451.5]; [MH$^+$=452]

EXAMPLE 57
(RS)-N-[2-Mercapto-5-methoxycarbontylpentanoyl]-$_L$-leucyl-$_L$-phenylalanine N-methyl amide
From example 7 (0.32 g), as a colourless solid (0.15 g).
TLC R$_f$ 0.29 (5% MeOH—CH$_2$Cl$_2$)

EXAMPLE 58
(RS)-N-[2-Mercapto-6-methoxycarbontylhexanoyl]-$_L$-leucyl-$_L$-phenylalanine N-methyl amide
From example 8 (0.31 g), as a colourless solid (0.22 g).
TLC R$_f$ 0.30 (5% MeOH—CH$_2$Cl$_2$)

EXAMPLE 59
(RS)-N-[2-Mercapto-4-phthalimidobutanoyl]-$_L$-leucyl-$_L$-phenylalanine N-methyl amide
From example 25 (0.20 g), as a pale yellow solid (0.12 g).
$C_{28}H_{34}N_4O_5S$ [538.6]; [MH$_2^+$=540]

EXAMPLE 60
(RS)-N-[2-Mercapto-5-phthalimidopentanoyl]-$_L$-leucyl-$_L$-phenylalanine N-methyl amide
From example 26 (0.2 g), a a colourless solid (0.18 g).
TLC R$_f$ 0.41 (5% MeOH—CH$_2$Cl$_2$)

EXAMPLE 61
(RS)-N-[2-Mercapto-6-phthalimidopentanoyl]-$_L$-leucyl-$_L$-phenylalanine N-methyl amide
From example 27 (0.15 g), as a pale yellow solid (0.12 g).
TLC R$_f$ 0.25 (10% MeOH—CH$_2$Cl$_2$)

EXAMPLE 62
(RS)-N-[2-Mercapto-5-phthalimidopentanoyl]-$_L$-leucyl-$_L$-tryptophanN-methyl amide
From example 9 (250 mg), as a pale yellow foam (222 mg, 96%).
$C_{31}H_{37}N_5O_5S$ [591.7]; [MH$^+$=592]

EXAMPLE 63
(RS)-N-[2-Mercapto-6-methoxycarbonylhexanoyl]-$_L$-leucyl-$_L$-trypotophan N-methyl amide
From example 10 (330 mg), as a colourless foam (300 mg, 98%).
$C_{26}H_{38}N_4O_5S$ [518.7]; [MH$^+$=519]

EXAMPLE 64
(S)-N-[2-Mercapto-5-phthalimidopentanoyl]-$_L$-(S-methyl)cysteinyl-$_L$-tryptophan N-methyl amide
Was prepared by the procedure described previously for examples 28 and 48, from intermediate 119 and intermediate 124.
$C_{29}H_{32}N_5O_5S_2$ [595.7]; [MH$^+$=596]

EXAMPLE 65
(RS)-N-[2-Mercapto-3-phthalimidopentanoyl]-$_L$-leucyl-$_L$-phenylalanine N-methyl amide
Was prepared by the procedure described previously for example 39 via intermediate 43, from intermediate 125 and $^L$-leucyl-$_L$-phenylalanine N-methyl amide.
$C_{27}H_{32}N_4O_5S$ [524.6]; [MH$^+$=525]

EXAMPLE 66
(RS)-N-[2-Mercapto-4-succinimidobutanoyl]-$_L$-leucyl-$_L$-phenylalanine N-methyl amide
Was prepared by the procedure described previously for examples 28 and 48, from intermediate 123 and $_L$-leucyl-$_L$-phenylalanine N-methly amide.
$C_{24}H_{34}N_4O_5S$ [490.6]; [MH$^+$=491]

EXAMPLE 67
(RS)-N-[2-Mercapto-4-succinimidobutanoyl]-(S)-propylglycinyl-$_L$-phenylalanine N-methyl amide
Was prepared by the procedure described previously for examples 28 and 48, from intermediate 123 and intermediate 113.
$C_{23}H_{31}N_4O_5S$ [475.6]; [MH$^+$=476]

EXAMPLE 68
(RS)-N-[2-Mercapto-4-succinimidobutanoyl]-$_L$-(S-methyl)cysteinyl-$_L$-tert-leucine N-methyl amide
Was prepared by the procedure described previously for examples 28 and 48, from intermediate 123 and intermediate 114.
$C_{19}H_{32}N_4O_5S_2$ [460.6]; [MH$^+$=461]

EXAMPLE 69
(RS)-N-[2-Mercapto-4-succinimidobutanoyl]-$_L$-(S-methyl)cysteinyl-$_L$-tryptophan N-methyl amide
Was prepared by the procedure described previously for examples 28 and 48, from intermediate 123 and intermediate 124.
$C_{24}H_{31}N_5O_5S_2$ [533.7]; [MH$^+$=534]

EXAMPLE 70
(RS)-N-[2-Mercapto-4-succinimidobutanoyl]-$_L$-(S-methyl)cysteinyl-$_L$-phenylalanine N-methyl amide
Was prepared by the procedure described previously for examples 28 and 48, from intermediate 123 and intermediate 111.
$C_{23}H_{30}N_4O_5S_2$ [506.6]; [MH$^+$=507]

EXAMPLE 71
(RS)-N-[2-Mercapto-4-succinimidobutanoyl]-$_L$-(O-methyl)serinyl-$_L$-tert-leucine N-methyl amide
Was prepared by the procedure described previously for examples 28 and 48, from intermediate 123 and intermediate 115.
$C_{19}H_{32}N_4O_5S$ [444.5]; [MH$^+$=445]

EXAMPLE 72
(RS)-N-[2-Mercapto-4-succinimidobutanoyl]-$_L$-leucyl-$_L$-tert-leucine N-methyl amide Was prepared by the procedure described previously for examples 28 and 48, from intermediate 123 and intermediate 116.

$C_{21}H_{36}N_4O_5S$ [456.6]; [MH$^+$=457]

EXAMPLE 73
(RS)-N-[2-Mercapto-6-carboxyhexanoyl]-$_L$-leucyl-$_L$-tryptophan N-methyl amide Was prepared by hydrolysis of example 10.

$C_{25}H_{36}N_4O_5S$ [504.7]; [MH$^+$=505]

EXAMPLE 74
(R)-N-[2-Acetylmercapto-6-methoxycarbonylhexanoyl]-$_L$-leucyl-$_L$-trypophan N-methyl amide Was prepared by separation of the 1:1 mixture of diastereoisomers present in example 10 by flash column chromatography.

$C_{26}H_{38}N_4O_5S$ [518.7]; [MH$^+$=519]

EXAMPLE 75
(S)-N-[2-Acetylmercapto-6-methoxycarbonylhexanoyl]-$_L$-leucyl-$_L$-trypophan N-methyl amide Was prepared by separation of the 1:1 mixture of diastereoisomers present in example 10 by flash column chromatography.

$C_{26}H_{38}N_4O_5S$ [518.7]; [MH$^+$=519]

EXAMPLE 76
(R)-N-[2-Acetylmercapto-5-phthalimidopentanoyl]-$_L$-leucyl-$_L$-trypophan N-methyl amide Was prepared by separation of the 1:1 mixture of diastereoisomers present in example 9 by flash column chromatography.

$C_{31}H_{37}N_5O_5S_2$ [591.7]; [MH$^+$=592]

EXAMPLE 77
(R)-N-[2-Acetylmercapto-5-methoxycarbonylhexanoyl]-$_L$-leucyl-$_L$-phenylalanine N-methyl amide Was prepared by separation of the 1:1 mixture of diastereoisomers present in example 7 by flash column chromatography.

$C_{25}H_{36}N_4O_5S$ [504.7]; [MH$^+$=505]

EXAMPLE 78
(R)-N-[2-Mercapto-6-(methylamino)carbonylhexanoyl]-$_L$-leucyl-$_L$-phenylalanine N-methyl amide Was prepared by hydrolysis of example 8.

$C_{24}H_{38}N_4O_4S$ [478.6]; [MH$^+$=479]

EXAMPLE 79
(RS)-N-[2-Mercapto-6-(amino)carbonylhexanoyl]-$_L$-leucyl-$_L$-phenylalanine N-methyl amide Was prepared by hydrolysis of example 8.

$C_{23}H_{36}N_4O_4S$ [464.6]; [MH$^+$=465]

EXAMPLE A
Collagenase inhibition activity

The potency of compounds of general formula (I) to act as inhibitors of collagenase was determined by the procedure of Cawston and Barrett, (Anal. Biochem., 99:340–345, 1979) whereby a 1 mM solution of the inhibitior being tested or dilutions thereof was incubated at 37° C. for 16 hours with collagen and collagenase (buffered with 50 mM Tris, pH 7.6 containing 5 mM CaCl$_2$, 0.05% Brij 35, 60 mM NaCl and 0.02% NaN$_3$). The collagen was acetylated $^3$H or $^{14}$C-collagen prepared by the method of Cawston and Murphy (Methods in Enzymology, 80:711, 1981). The choice of radiolabel did not alter the ability of collagenase to degrade the collagen substrate. The samples were centrifuged to sediment undigested collagen and an aliquot of the radioactive supernatant removed for assay on a scintillation counter as a measure of hydrolysis. The collagenase activity in the presence of 1 mM inhibitor, or a dilution thereof, was compared to activity in a control devoid of inhibitior and the results reported as that inhibitor concentration effecting 50% inhibition of the collagnease (IC$_{50}$).

EXAMPLE B
Stromelysin inhibition activity

The potency of compounds of general formula (I) to act as inhibitors of stromelysin was determined using the prodecure of Nagase et al (Methods in Enzymology Vol 254, 1994), whereby a 0.1 mM solution of the inhibitor being tested or dilutions thereof was incubated at 37° C. for 16 hours with stromelysin and $^3$H transferrin (buffered with 50 mM Tris, pH 7.6 containing 10 mM CaCl$_2$, 150M NaCl, 0.05% Brij, 35, and 0.02% NaN$_3$). The tansferin was carboxymethylated with $^3$H iodoacetic acid. The stromelysin activity in the presence of 1 mM, or a dilution thereof, was compared to activity in a control devoid of inhibitor and the results reported as that inhibitor concentration effecting 50% inhibition of the stromelysin (IC$_{50}$)

EXAMPLE C
Gelatinase inhibition activity

The potency of the compounds of general formula (I) to act as inhibitors of gelatinase was determined using the procedure of Harris & Krane (Biochem Biophys. Acta, 258:566–576, 1972), whereby a 1 mM solution of the inhibitior being tested or dilutions thereof was incubated at 37° C. for 16 hours with gelatinase and heat denatured $^3$H or $^{14}$C-acetylated collagen (buffered with 50 mM Tris, pH 7.6 containing 5 mM CaCl$_2$, 0.05% Brij 35 and 0.02% NaN$_3$). The $^3$H or $^{14}$C gelatin was prepared by denaturing $^3$H or $^{14}$C-collagen produced according to the method of Cawston and Murphy (Methods in Enzymology, 80:711, 1981) by incubation at 60° C. for 30 minutes. Undigested gelatin was precipitated by addition of trichloroacetic acid and centrifugaion. The gelatinase activity in the presence of 1 mM, or dilution thereof, was compared to the activity in a control devoid of inhibitior and results reported as that inhibitor-concentraion effecting 50% inhibition of the gelatinase (IC$_{50}$).

EXAMPLE D
Inhibition of TNFα production

The potency of the compounds of general formula (I) to act as inhibitors of the production of TNFa was determined using the floowing procedure. A 1 mM solution of the inhibitor being tested or dilutions thereof was incubated at 37° C. in an atmosphere of 5% CO$_2$ with THP-1 cells (human monocytes) suspended in RPM1 1640 medium and 20 μM β-mercaptoethanol at a cell densiy of 1×10$^6$/ml and stimulated with 5 μg/ml final concentraion of LPS. After 18 hours the supernatant is assayed for the levels of TNFα using aconmmercially available ELISA kit (R & D Systems).

The activity in the presence of 0.1 mM inhibitior or dilutions thereof was compared to activity in a control devoid of inhibitior and results reported as that inhibitor concentraion effecting 50% inhibition of the production of TNFa.

EXAMPLE E
Adjuvant arthritic rat model

Compounds of general formula (I) were evaluated in an adjuvant arthritis model in the rat based on the methods employed by B. B. Newbould (1963), Br. J. Pharmacol, 21, 127–136 and C. M. Pearson and F. D. Wood (1959), Arthritis Rheum, 2, 440–459. Briefly male Wistar rats (180–200 g) were injected at the base of the tail with Freund's adjuvant. Twelve days later the responding animals were randomised into experimental groups. Compounds of general formula (I) were dosed either orally as a suspension in 1% methyl cellulose or intraperitoneally in 0.2% carboxymethylcellulose from day 12 to the end of the experiment on day 22. Hind paw volumes were measured every two days from day 12 onwards and X-rays were taken of the hind feet on completion of the experiment. Results were expressed as the percent increase of foot volume over day 12 values.

EXAMPLE F
Mouse ovarian carcinoma xenograft model

Compounds of general formula (I) were evaluated in an ovarian carcinoma xenograft model of cancer, based on that described by B. Davies et al (1993), Cancer Reasearch, 53, 2087–2091 This model, in brief, consists of inoculating female nu/nu mice with $1 \times 10^9$ OVCAR3-icr cells into the peritoneal cavity. Compounds of general formula (I) are administered by theoral route as a suspension in 1% methyl cellulose or intraperitoneally as a suspension in phosphate buffered saline in 0.01% Tween-20. At the conculusion of the experiment (4–5 weeks) the number of peritoneal cells are counted and any solid tumour deposits weighted. In some experiments tumour development is monitored by measurement of tumour specific antigens.

EXAMPLE G
Rat mammary carcinoma model

Compounds of general formula (I) were evaluated in a HOSP.1 rat mammary carcinoma model of cancer (S. Eccles et al (1995), Cancer Research, in press). This model consists of the intravenous inoculation of female CBH/cbi rats with $2 \times 10^4$ tumour cells into the jugular vein. Compounds of general formula (I) are administered by the oral route as a suspension in 1% methyl cellulose or intraperitoneally as a suspension in phosphate buffered saline in 0.01% Tween-20. At the conclusion of the experiment (4–5 weeks) the animals were killed, the lungs were removed and individual tumours counted after 20 hours fixation in Methacarn.

We claim:

1. A compound of general formula (I):

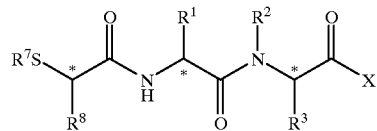

(I)

wherein:

$R^1$ is $C_{1-6}$ alkyl, $C_{2-6}$ alkenyl, —$C_{1-6}$ alkyl-aryl, aryl, —$C_{1-6}$ alkyl-heteroaryl, heteroaryl or —$C_{1-6}$ alkyl-$AR^9$ where A represents O, $NR^9$ or $S(O)_m$ where m=0,2, and $R^9$ is H, $C_{1-4}$ alkyl, aryl heteroryl, —$C_{1-4}$ alkyl-aryl or —$C_{1-4}$ alkyl-heteroaryl; if $A=NR^9$ the groups $R^9$ may be the same or different;

$R^2$ is H or $C_{1-6}$ alkyl;

$R^3$ is $[Alk]_n R^6$ where Alk is $C_{1-6}$ alkyl or $C_{2-6}$ alkenyl or n is zero or 1;

X is $NR^4R^5$ where either $R^4$ is hydrogen or $C_{1-6}$ alkyl optionally substituted by amino ($NH_2$), aryl, arylamino, protected amino, di($C_{1-6}$ alkyl)amino, momo($C_{1-6}$ alkyl)amino, $CO_2H$, protected carboxyl, carbomoyl, mono($C_{1-6}$alkyl)carbamoyl or di($C_{1-6}$alkyl)carbamoyl, and $R^5$ is hydrogen or $C_{1-6}$ alkyl; or $NR^4R^5$ forms a ring such as pyrrolidino, piperidino or morpholino;

$R^7$ is hydrogen or $R^{10}CO$ where $R^{10}$ is $C_{1-4}$ alkyl, —$C_{1-4}$ alkyl-aryl, —$C_{1-4}$ alkyl-heteroaryl, cyclo ($C_{3-6}$)alkyl, —$C_{1-4}$ alkyl-cyclo($C_{3-6}$)alkyl, $C_{2-6}$ alkenyl, —$C_{2-6}$ alkenyl-aryl, aryl, or heteroaryl;

$R^8$ is aryl substituted with $R^{11}$, heteroaryl substituted with $R^{11}$, $C_{1-4}$ alkyl-$R^{11}$, —$C_{1-4}$ alkyl-aryl substituted with $R^{11}$, —$C_{1-4}$ alkyl-heteroaryl substituted with $R^{11}$, cyclo ($C_{3-6}$)alkyl substituted with $R^{11}$, cyclo($C_{3-6}$)alkenyl substituted with $R^{11}$, —$C_{1-4}$ alkyl-cyclo($C_{3-6}$)alkyl substituted with $R^{11}$, or any of the three groups

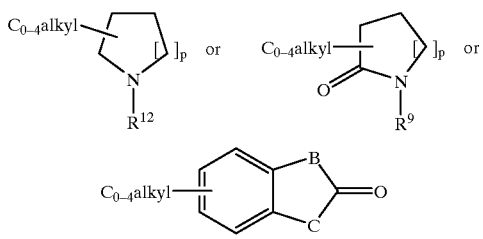

where p is 1 or 2 and B and C are independently selected from O, S, $C(R^9)_2$ and $NR^9$;

$R^6$ is $AR^9$, cyclo($C_{3-6}$)alkyl, cyclo($C_{3-6}$)alkenyl, $C_{1-6}$ alkyl, —$C_{1-6}$ alkoxy-aryl, benzyloxyaryl, aryl, heteroaryl, —$C_{1-3}$ alkyl-heteroaryl, —$C_{1-3}$ alkyl-aryl, —$C_{1-6}$ alkyl-$COOR^9$, —$C_{1-6}$ alkyl-NHR, CONHR, $NHCO_2R$, $NHSO_2R$ or NHCOR, R being defined as for $R^{10}$;

$R^{11}$ is $COR^{13}$, succinimido or phthalimido;

$R^{12}$ is H or $COR^9$, $CO_2R^9$ (where $R^9$ is not H), $CONHR^9$ or $SO_2R^9$ (where $R^9$ is not H); and $R^{13}$ is OH, $OC_{1-4}$ alkyl, O—$C_{1-4}$ alkyl-aryl, $N(R^9)_2$ (in which the $R^9$s are the same or different), $C_{1-4}$ alkyl, aryl, heteroaryl, —$C_{1-4}$ alkyl-aryl or —$C_{1-4}$ alkyl-heteroaryl;

the compound being in the form of a non-salt, salt, solvate, or hydrate.

2. A compound of claim 1, wherein $R^1$ is $C_{1-6}$ alkyl or $C_{1-6}$ alkyl-$AR^9$, where A is $S(O)_m$, $NR^9$, or O; and m=0, 1, or 2; and $R^9$ is H, $C_{1-4}$ alkyl or aryl.

3. A compound of claim 1, wherein $R^3$ is $[Alk]_m R^6$ where n=0 or 1, Alk is $C_{1-6}$ alkyl, and $R^6$ is $C_{1-6}$ alkyl, —$C_{1-3}$ alkyl-aryl, —$C_{1-3}$ alkyl-heteroaryl, or $AR^9$.

4. A compound of claim 1, wherein $R^4$ is H.

5. A compound of claim 1, wherein X is pyrrolidino, piperidino, or morpholino.

6. A compound of claim 1, wherein $R^7$ is H or $(C_{1-4})$ carbonyl.

7. A compound of claim 1, wherein $R^8$ is $C_{1-4}$ alkyl-$R^{11}$ or cyclo $(C_{3-6})$alkyl-$R^{11}$, $R^{12}$ is $COR^9$, $CO_2R^9$ (provided $R^9$ is not H) or $SO_2R^9$ (provided $R^9$ is not H), and $R^{13}$ is OH, $OC_{1-4}$ alkyl or $N(R^9)_2$.

8. A compound of claim 1, wherein $R^5$ is H or $C_{1-6}$ alkyl.

9. A compound of claim 8, wherein:

$R^1$ is alkyl, alkenyl, alkylaryl, aryl or alkyl-$AR^9$ and $R^9$ is alkyl, aryl or heteroaryl;

$R^7$ is H or $R^{10}CO$ where $R^{10}$ is alkyl, alkylaryl, cycloalkyl, cycloalkylalkyl, alkenyl or alkenylaryl;

$R^8$ is aryl substituted with $R^{11}$, heteroaryl substituted with $R^{11}$, —$C_{1-4}$ alkylaryl substituted with $R^{11}$, cyclo($C_{3-6}$)

alkyl substituted with $R^{11}$, cyclo($C_{3-6}$)alkenyl substituted with $R^{11}$ or —$C_{1-4}$ alkylcyclo($C_{3-6}$)alkyl substituted with $R^{11}$, alkyl-$R^{11}$ or any of the said three groups;

$R^6$ is cycloalkyl, cycloalkenyl, alkyl, benzyl, alkoxybenzyl or 3- indolylmethyl; and $R^{13}$ is OH, Oalkyl, Oalkylaryl, N($R^9$)$_2$ alkyl, aryl or alkylaryl.

10. A compound of claim 1, selected from the group consisting of

N-[2,3-bis-Acetylmercaptopropanoyl]-L-leucyl-L-phenylalanine N-methylamide

N-[2-Acetylmercapto-3-methoxycarbonylpropanoyl]-L-leucyl-L-phenylalanine N-methylamide N-[2-Acetylmercapto-4-methoxycarbonylpropanoyl]-L-leucyl-L-phenylalanine N-methylamide N-[2-Acetylmercapto-5-methoxycarbonylpropanoyl]-L-leucyl-L-phenylalanine N-methylamide N-[2-Acetylmercapto-6-methoxycarbonylhexanoyl]-L-leucyl-L-phenylalanine N-methylamide N-[2-Acetylmercapto-4-phthalimidobutanoyl]-L-leucyl-L-phenylalanine N-methylamide N-[2-Acetylmercapto-5-phthalimidopentanoyl]-L-leucyl-L-phenylalanine N-methylamide N-[2-Acetylmercapto-6-phthalimidohexanoyl]-L-leucyl-L-phenylalanine N-methylamide N-[2,3-bis-Mercaptopropanoyl]-L-leucyl-L-phenylalanine N-methylamide N-[2-Mercapto-3-methoxycarbonylpropanoyl]-L-leucyl-L-phenylalanine N-methylamide N-[2-Mercapto-4-methoxycarbonylbutanoyl]-L-leucyl-L-phenylalanine N-methylamide N-[2-Mercapto-5-methoxycarbonylpentanoyl]-L-leucyl-L-phenylalanine N-methylamide N-[2-Mercapto-6-methoxycarbonylhexanoyl]-L-leucyl-L-phenylalanine N-methylamide N-[2-Mercapto-4-phthalimidobutanoyl]-L-leucyl-L-phenylalanine N-methylamide N-[2-Mercapto-5-phthalimidopentanoyl]-L-leucyl-L-phenylalanine N-methylamide and N-[2-Mercapto-6-phthalimidohexanoyl]-L-leucyl-L-phenylalanine N-methylamide.

11. A compound of claim 1, selected from the group consisting of

N-[2-Acetylmercapto-5-methoxycarbonylpentanoyl]-L-leucyl-L-phenylalanine N-methylamide N-[2-Acetylmercapto-6-methoxycarbonylhexanoyl]-L-leucyl-L-phenylalanine N-methylamide N-[2-Acetylmercapto-6-methoxycarbonylhexanoyl]-L-valinyl-L-phenylalanine N-methylamide N-[2-Acetylmercapto-6-methoxycarbonylhexanoyl]-L-leucyl-L-tryptophan N-methylamide N-[2-Acetylmercapto-5-phthalimidopentanoyl]-L-leucyl-L-phenylalanine N-methylamide N-[2-Acetylmercapto-5-phthalimidopentanoyl]-L-valinyl-L-phenylalanine N-methylamide N-[2-Acetylmercapto-5-phthalimidopentanoyl]-L-leucyl-L-tryptophan N-methylamide N-[2-Acetylmercapto-5-phthalimidopentanoyl]-L-leucyl-L-[β-(4-thiazolyl)]alanine N-methylamide N-[2-Acetylmercapto-5-phthalimidopentanoyl]-L-leucyl-L-[β-(2-pyridyl)]alanine N-methylamide N-[2-Acetylmercapto-5-phthalimidopentanoyl]-L-leucyl-5-methyl-L-glutamic acid N-methylamide N-[2-Acetylmercapto-6-phthalimidohexanoyl]-L-leucyl-L-phenylalanine N-methylamide N-[2-Acetylmercapto-2-(3-phthalimido)phenylacetyl]-L-leucyl-L-phenylalanine N-methylamide N-[2-Mercapto-5-methoxycarbonylpentanoyl]-L-leucyl-L-phenylalanine N-methylamide N-[2-Mercapto-6-methoxycarbonylhexanoyl]-L-leucyl-L-phenylalanine N-methylamide N-[2-Mercapto-6-methoxycarbonylhexanoyl]-L-leucyl-L-trypotophan N-methylamide N-[2-Mercapto-5-phthalimidopentanoyl]-L-leucyl-L-phenylalanine N-methylamide N-[2-Mercapto-6-phthalimidopentanoyl]-L-leucyl-L-tryptophan N-methylamide N-[2-Mercapto-5-phthalimidopentanoyl]-L-leucyl-L-[β-(4-thiazolyl)]alanine N-methylamide N-[2-Mercapto-5-phthalimidopentanoyl]-L-leucyl-L-[β-(2-pyridyl)]alanine N-methalamide and N-[2-Mercapto-5-phthalimidopentanoyl]-L-leucyl-5-methyl-L-glutamic acid N-methylamide and N-[2-Mercapto-6-phthalimidohexanoyl]-L-leucyl-L-phenylalanine N-methylamide.

12. A compound of claim 1, wherein $R^1$ is —$CH_2SCH_3$.

13. A compound of claim 12, selected from the group consisting of

N-[2-(Acetylmercapto)-5-phthalimidopentanoyl]-(S-methyl)-L-cyseinyl-L-phenylalanine N-methyl amide N-[2-Mercapto-5-phthalimidopentanoyl]-L-(S-methyl) cysteinyl-L-tryptophan N-methyl amide N-[2-Mercapto-4-succinimidobutanoyl]-L-(S-methyl) cysteinyl-L-tert-leucine N-methyl amide N-[2-Mercapto-4-succinimidobutanoyl]-L-(S-methyl) cysteinyl-L-tryptophan N-methyl amide and N-[2-Mercapto-4-succinimidobutanoyl]-L-(S-methyl) cysteinyl-phenylalanine N-methyl amide.

14. A compound of claim 1, wherein $R^3$ is tert-butyl or —$C(CH_3)_2S(O)_{0-2}CH_3$.

15. A compound of claim 14, selected from the group consising of

N-[2-(Acetylmercapto)-5-phthalimido]pentanoyl-L-leucyl-(S)-tert-leucine N-methyl amide N-[2-(Acetylmercapto)-5-phthalimido]pentanoyl-L-leucyl-(R)-penicillamine N-methyl amide N-[2-(Acetylmercapto)-5-phthalimido]pentanoyl-L-leucyl-(R)-(S-methyl)-penicillamine N-methyl amide N-[2-(Acetylmercapto)-5-phthalimido]pentanoyl-L-leucyl-(R)-(2,2-dimethyl-2-methanesulphonyl)alanine N-methyl amide N-[2-(Acetylmercapto)-5-phthalimido]pentanoyl-L-leucyl-(R)-(2,2-dimethyl-2-methanesulphinyl)alanine N-methyl amide N-[2-(Acetylmercapto)-5-phthalimido]pentanoyl-L-leucyl-(R)-(S)-tert-leucine N-methyl amide N-[2-Mercapto-5-phthalimido]pentanoyl-L-leucyl-(R)-(S-methyl)-penicillamine N-methyl amide N-[2-Mercapto-5-phthalimido]pentanoyl-L-leucyl-(S)-tert-leucine N-methyl amide and N-[2-Mercapto-4-succinimidobutanoyl]-L-leucyl-L-tert-leucine N-methyl amide.

16. A compound of claim 1, in the form of a single enantimoer or diastereomer, or a mixture of such isomers.

17. A pharmaceutiacl composition for use in therapy, comprising a compound of claim 1, and a pharmaceutically-acceptable diluent or carrier.

18. A method for the treatment of a condition associated with matrix metalloproteinases or that is mediated by TNFα, said method comprising administering an effective amount of the compound of claim 1 to a person or animal in need of such treatment.

19. The method according to claim 18, wherein the condition is selected from the group consisting of inflammation and inflammatory diseases, tissue degeneration, periodontal disease, ophthalmological disease, dermatological disorders, fever, cardiovascular effects, haemorrhage, coagulation and acute phase response, cachexia and anorexia, acute infection, HIV infection, shock states, graft versus host reactions,autoimmune disease, reperfusion injury, meningitis and migraine.

20. The method according to claim 19, wherein the condition is selected from the group consisting of tumour growth, angiogenesis, tomour invasion and spread, metastases, malignant ascites and malignant pleural effusion.

21. The method according to claim 19, wherein the condition is selected from the group consisting of rheumatoid arthritis, osteosrthritis, osteoporosis, asthma, multiple sclerosis, neurodegeneration, Alzheimer's disease, atherosclerosis, stroke, vasculitis, Crohn's disease and ulcerative colitis.

22. The method according to claim 19, wherein the condition is selected from the group consisting of corneal ulceration, retinopathy and surgical wound healing.

23. The method according to claim 19, wherein the condition is selected from the group consisting of psoriasis, atopic dermatitis chronic ulcers and epidermolysis bullosa.

24. The method according to claim 19, wherein the condition is periodonititis or gingivitis.

* * * * *

UNITED STATES PATENT AND TRADEMARK OFFICE
CERTIFICATE OF CORRECTION

PATENT NO.    :   5,994,312

DATED         :   November 30, 1999

INVENTOR(S)   :   John Montana, Andrew Douglas Baxter, David Alan Owen, Robert John Watson, Neil Phillipson It is certified that error appears in the above-identified patent and that said Letters Patent is hereby corrected as shown below:

Column 45, line 59: "alkyl, aryl heteroryl" should read --alkyl, aryl, heteroaryl--.

Column 45, line 67: "momo ($C_{1-6}$" should read --mono ($C_{1-6}$--.

Column 46, line 1: "carbomoyl" should read --carbamoyl--.

Column 46, line 54: "($C_{1-4}$)" should read --($C_{1-4}$ alkyl)--.

Column 46, line 65: "cycloalkylakyl" should read --cycloalkylalkyl--.

UNITED STATES PATENT AND TRADEMARK OFFICE
CERTIFICATE OF CORRECTION

PATENT NO. : 5,994,312

DATED : November 30, 1999

INVENTOR(S) : John Montana, Andrew Douglas Baxter, David Alan Owen, Robert John Watson, Neil Phillipson It is certified that error appears in the above-identified patent and that said Letters Patent is hereby corrected as shown below:

Column 48, line 57: "enantimoer" should read --enantiomer--.

Column 49, line 10: "tomour invasion" should read --tumour invasion--.

Signed and Sealed this

Tenth Day of April, 2001

Attest:

NICHOLAS P. GODICI

Attesting Officer

Acting Director of the United States Patent and Trademark Office